US010603068B2

(12) United States Patent
Schneider et al.

(10) Patent No.: US 10,603,068 B2
(45) Date of Patent: *Mar. 31, 2020

(54) TISSUE-REMOVING CATHETER FOR BODY LUMEN

(71) Applicant: Covidien LP, Mansfield, MA (US)

(72) Inventors: Lucas Schneider, Champlin, MN (US); Benjamin Fruland, Blaine, MN (US); Bryan Ladd, Minneapolis, MN (US)

(73) Assignee: Covidien LP, Mansfield, MA (US)

( * ) Notice: Subject to any disclaimer, the term of this patent is extended or adjusted under 35 U.S.C. 154(b) by 523 days.

This patent is subject to a terminal disclaimer.

(21) Appl. No.: 15/378,379

(22) Filed: Dec. 14, 2016

(65) Prior Publication Data

US 2017/0086873 A1     Mar. 30, 2017

Related U.S. Application Data

(63) Continuation of application No. 14/101,920, filed on Dec. 10, 2013, now Pat. No. 9,549,718.

(60) Provisional application No. 61/736,175, filed on Dec. 12, 2012.

(51) Int. Cl.
*A61B 17/3207* (2006.01)
*A61B 17/00* (2006.01)

(52) U.S. Cl.
CPC .... *A61B 17/3207* (2013.01); *A61B 17/00234* (2013.01); *A61B 17/320758* (2013.01); *A61B 17/320783* (2013.01); *A61B 2017/00292* (2013.01); *A61B 2017/00318* (2013.01); *A61B 2017/320741* (2013.01); *A61B 2017/320775* (2013.01); *A61B 2017/320791* (2013.01)

(58) Field of Classification Search
None
See application file for complete search history.

(56) References Cited

U.S. PATENT DOCUMENTS

| | | |
|---|---|---|
| 4,290,427 A | 9/1981 | Chin |
| 4,631,052 A | 12/1986 | Kensey |
| 4,765,332 A | 8/1988 | Fischell et al. |
| 4,790,813 A | 12/1988 | Kensey |
| 4,926,858 A | 5/1990 | Gifford, III et al. |
| 4,950,277 A | 8/1990 | Farr |
| 5,026,383 A | 6/1991 | Nobles |
| 5,085,662 A | 2/1992 | Willard |
| 5,100,424 A | 3/1992 | Jang et al. |
| 5,123,904 A | 6/1992 | Shimomura et al. |
| 5,176,693 A | 1/1993 | Pannek, Jr. |
| 5,192,291 A | 3/1993 | Pannek, Jr. |

(Continued)

OTHER PUBLICATIONS

Japanese Office action for Application No. 2015-547429, dated Aug. 9, 2018, 40 pages.

*Primary Examiner* — Shaun L David

(57) ABSTRACT

A catheter for removing tissue from a body lumen include's a rotatable cutter. The cutter includes an annular cutting tip at the distal end portion of the cutter for removing tissue from the body lumen. An axial cavity is defined by an interior surface of the cutter and extends proximally from the annular cutting tip toward the proximal end portion of the cutter. An eccentric opening extends from the central cavity through the cutter to allow tissue removed from the body lumen by the annular cutting tip to pass proximally through the eccentric opening toward an interior passage of the catheter body. The offset opening is offset from the longitudinal axis of the cutter.

20 Claims, 34 Drawing Sheets

(56) References Cited

U.S. PATENT DOCUMENTS

| | | |
|---|---|---|
| 5,226,909 A | 7/1993 | Evans et al. |
| 5,242,460 A | 9/1993 | Klein et al. |
| 5,350,390 A | 9/1994 | Sher |
| 5,507,760 A | 4/1996 | Wynne et al. |
| 5,507,795 A | 4/1996 | Chiang et al. |
| 5,556,408 A | 9/1996 | Farhat |
| 5,569,277 A | 10/1996 | Evans et al. |
| 5,601,580 A | 2/1997 | Goldberg et al. |
| 5,620,456 A | 4/1997 | Sauer et al. |
| 5,776,156 A | 7/1998 | Shikhman |
| 5,857,982 A | 1/1999 | Milliman et al. |
| 6,053,923 A | 4/2000 | Veca et al. |
| 6,068,603 A | 5/2000 | Suziki |
| 6,110,127 A | 8/2000 | Suziki |
| 6,428,539 B1 | 8/2002 | Baxter et al. |
| 6,503,263 B2 | 1/2003 | Adams |
| RE38,018 E | 3/2003 | Anctil et al. |
| 6,579,298 B1 | 6/2003 | Bruneau et al. |
| RE38,335 E | 11/2003 | Aust et al. |
| 7,329,267 B2 | 2/2008 | Weber |
| 7,344,546 B2 | 3/2008 | Wulfman et al. |
| 7,485,125 B2 | 2/2009 | Sjostrom |
| 7,520,886 B2 | 4/2009 | Surti |
| 7,635,340 B2 | 12/2009 | Vetter et al. |
| 7,699,790 B2 | 4/2010 | Simpson |
| 7,862,518 B2 | 1/2011 | Parihar |
| 7,918,803 B2 | 4/2011 | Ritchart et al. |
| 7,927,784 B2 | 4/2011 | Simpson |
| 7,951,161 B2 | 5/2011 | Bonnette et al. |
| 1,981,128 A1 | 7/2011 | To et al. |
| 8,012,164 B1 | 9/2011 | Donohoe et al. |
| 8,052,704 B2 | 11/2011 | Olson |
| 8,062,316 B2 | 11/2011 | Patel et al. |
| 8,070,762 B2 | 12/2011 | Escudero et al. |
| 2003/0125758 A1 | 7/2003 | Simpson |
| 2004/0006358 A1 | 1/2004 | Wulfman et al. |
| 2007/0055259 A1 | 3/2007 | Norton et al. |
| 2007/0276419 A1 | 11/2007 | Rosenthal |
| 2007/0282358 A1 | 12/2007 | Remiszewski et al. |
| 2008/0045986 A1 | 2/2008 | To et al. |
| 2008/0065124 A1 | 3/2008 | Olson |
| 2008/0140104 A1 | 6/2008 | Bender et al. |
| 2010/0198240 A1 | 8/2010 | Simpson et al. |
| 2011/0004107 A1 | 1/2011 | Rosenthal et al. |
| 2011/0087258 A1 | 4/2011 | Sluss |
| 2011/0130777 A1 | 6/2011 | Zhang et al. |
| 2011/0144673 A1 | 6/2011 | Zheng et al. |
| 2011/0152906 A1 | 6/2011 | Escudero et al. |
| 2011/0190801 A1 | 8/2011 | Mark et al. |
| 2011/0301626 A1 | 12/2011 | To et al. |
| 2011/0306995 A1 | 12/2011 | Moberg |
| 2011/0313346 A1 | 12/2011 | Straub |

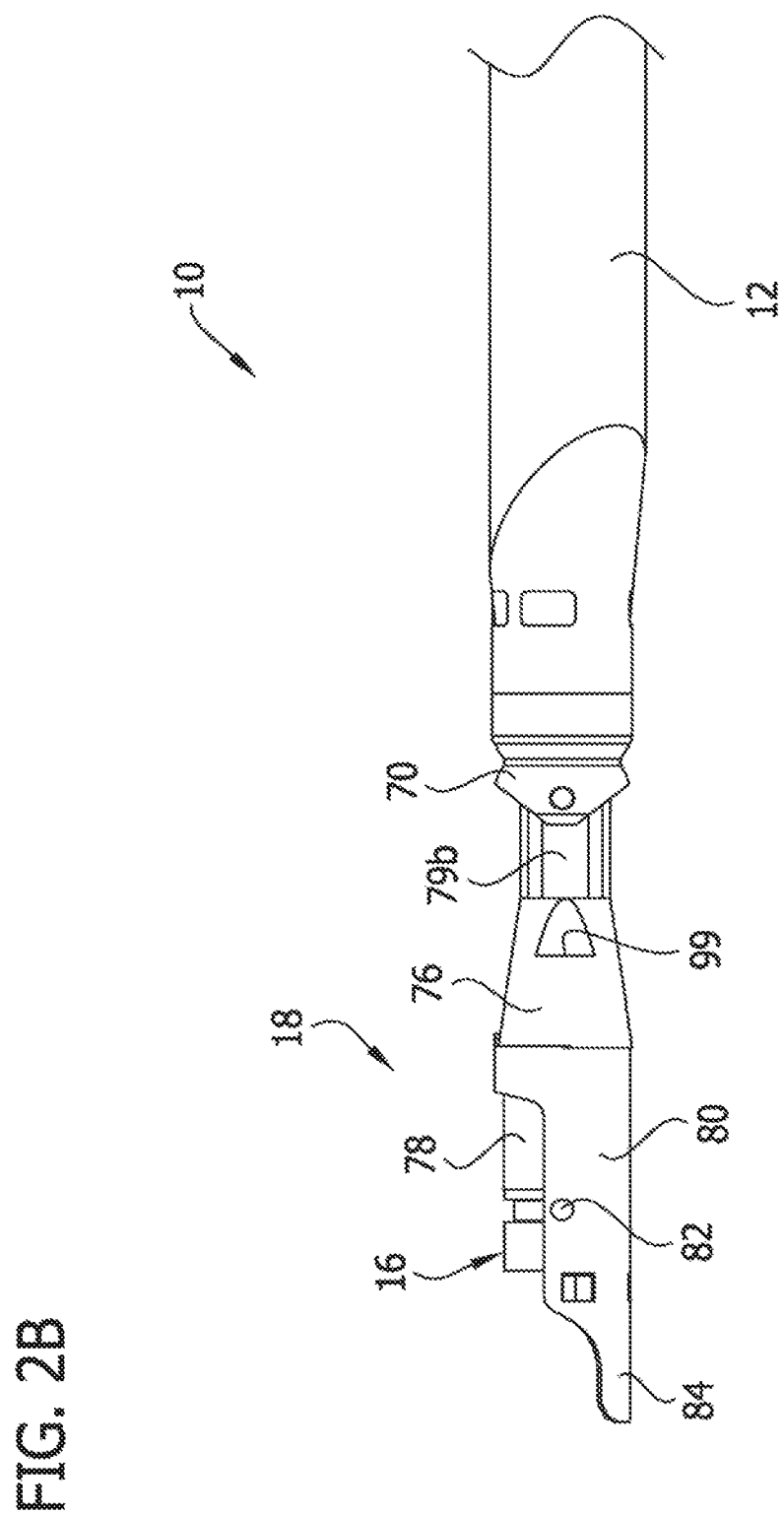

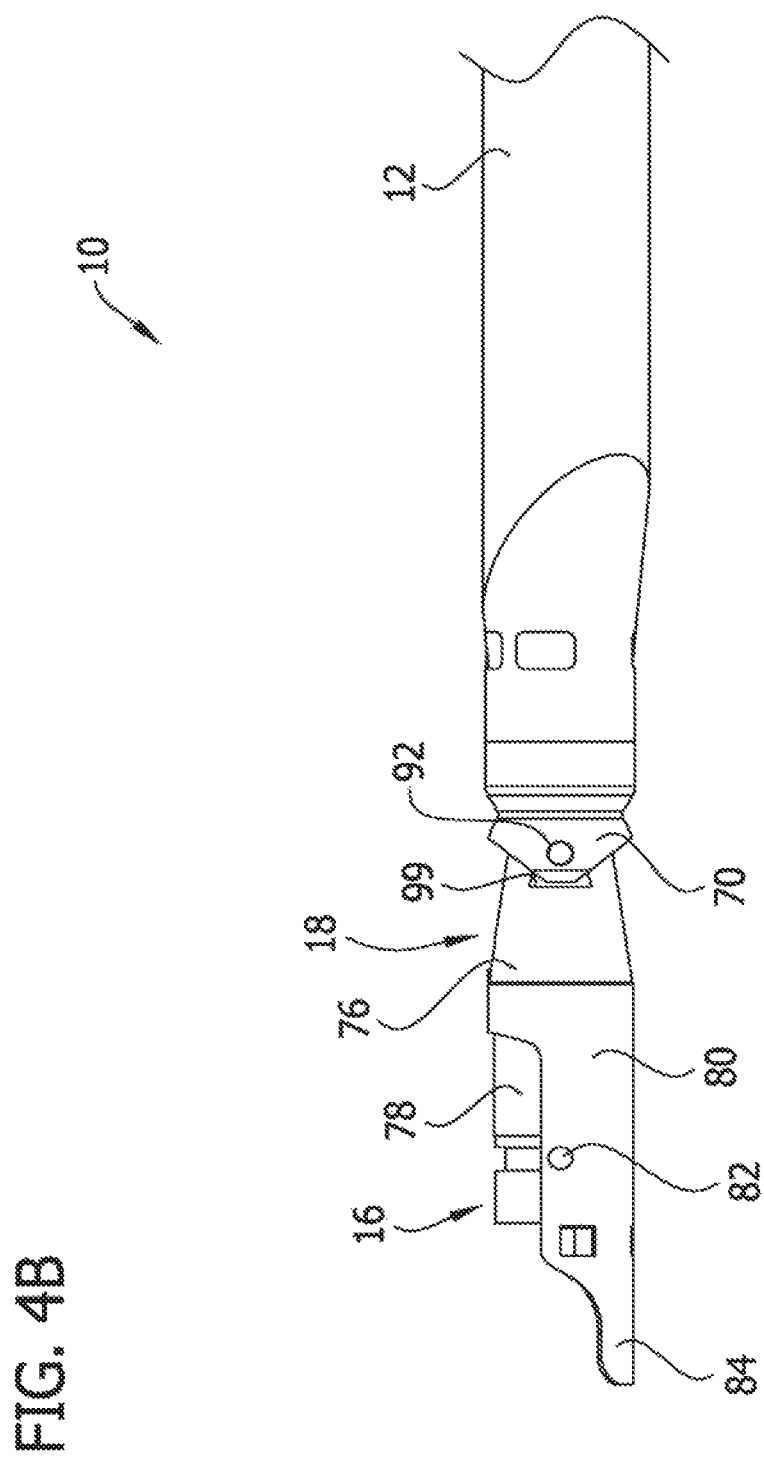

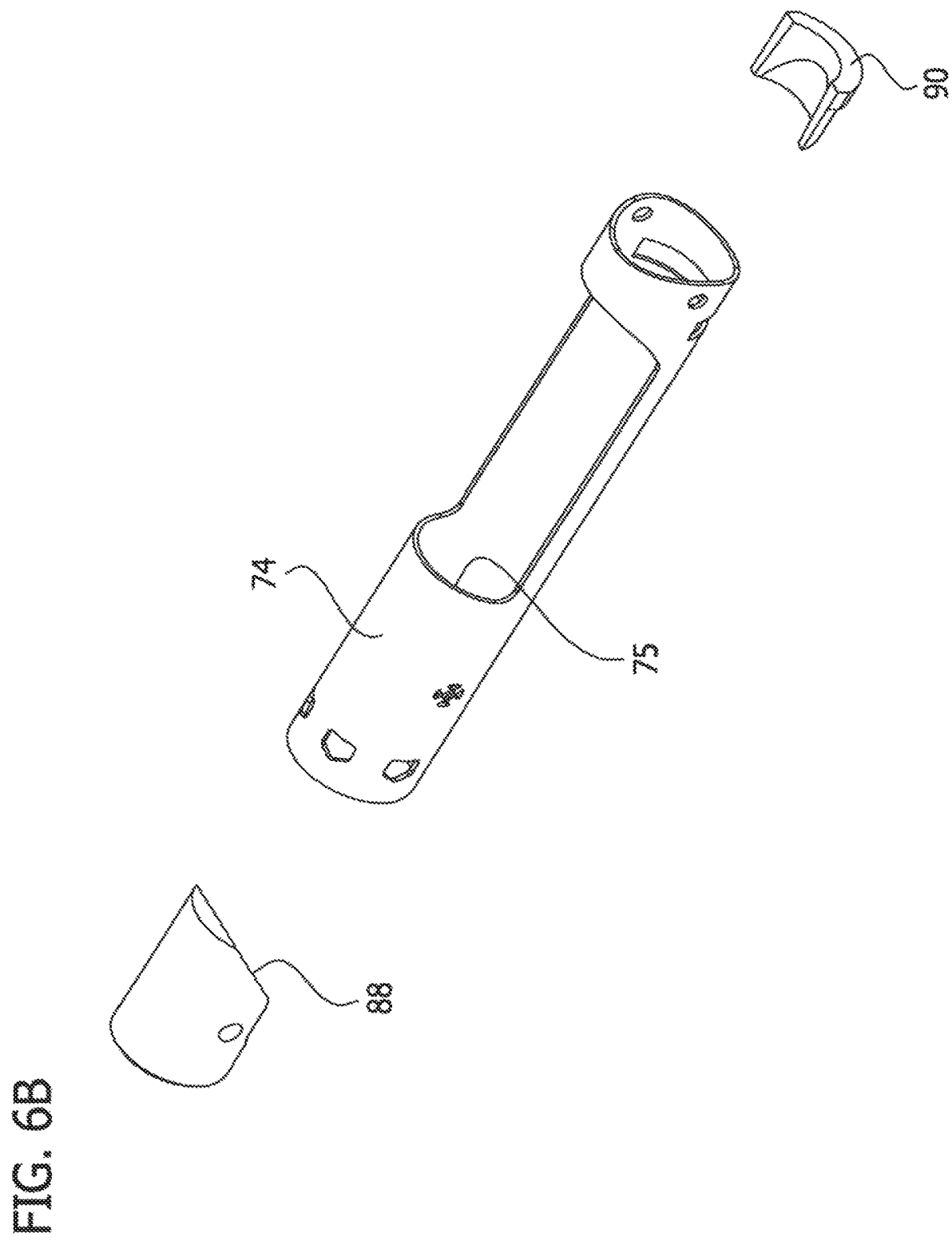

TISSUE-REMOVING CATHETER FOR BODY LUMEN

CROSS-REFERENCE TO RELATED APPLICATION

The present application is a continuation of U.S. application Ser. No. 14/101,920, filed Dec. 10, 2013, issued as U.S. Pat. No. 9,549,718, which claims priority to U.S. Provisional Application Ser. No. 61/736,169, filed Dec. 12, 2012, the entirety of each of which is hereby incorporated by reference in its entirety.

FIELD OF THE DISCLOSURE

The present invention generally relates to a tissue-removing catheter for a body lumen.

BACKGROUND

Vascular disease frequently arises from the accumulation of atheromatous material on the inner wafts of vascular lumens, particularly arterial lumens of the peripheral and other vasculature, especially peripheral arteries, resulting in a condition known as atherosclerosis. Atherosclerosis occurs naturally as a result of aging, but may also be aggravated by factors such as diet, hypertension, heredity, vascular injury, and the like. Atheromatous deposits can have widely varying properties, with some deposits being relatively soft and others being fibrous and/or calcified, in the latter case, the deposits are frequently referred to as plaque.

Vascular disease can be treated in a variety of ways, including drugs, bypass surgery, and a variety of catheter-based approaches, including those which rely on intravascular debulking or removal of the atheromatous or other material occluding a blood vessel. A variety of methods for cutting or dislodging material and removing such material from the blood vessel have been proposed, generally being referred to as atherectomy procedures. Atherectomy catheters intended to cut or excise material from the blood vessel lumen may employ a rotatable cutting blade (or other tissue-removing element) which can be advanced into or past the occlusive material in order to cut and separate such material from the blood vessel lumen.

It is desirous to provide catheters which can access small, tortuous regions of body lumens and which can remove tissue and/or other occluding materials from within body lumens in a controlled fashion. In one instance, it may be desired to provide atherectomy catheters which can facilitate capturing atheromatous materials. The catheters and methods for use in a variety of body lumens, including but not limited to coronary, peripheral; and other arteries, and other body lumens.

SUMMARY

In one aspect, a catheter generally comprises an elongate catheter body configured for insertion into a body lumen of a subject. The catheter body has opposite distal and proximal ends, a longitudinal axis extending between the distal and proximal ends, and an interior passage extending along the longitudinal axis. A cutter is located generally at the distal end of the catheter body. The cutter has a proximal end portion, a distal end portion, and a longitudinal axis extending between the proximal and distal end portions. The cutter is rotatable relative to the catheter body generally about its longitudinal axis. The cutter includes an annular cutting tip at the distal end portion of the cutter for removing tissue from the body lumen, an axial cavity defined by an interior surface of the cutter extending proximally from the annular cutting tip toward the proximal end portion of the cutter, and an eccentric opening extending from the central cavity through the cutter to allow tissue removed from the body lumen by the annular cutting tip to pass proximally through the eccentric opening toward the interior passage of the catheter body. The eccentric opening is offset from the longitudinal axis of the cutter body.

In another aspect, a catheter generally comprises an elongate catheter body configured for insertion into a body lumen of a subject. The catheter body has opposite distal and proximal ends, and a longitudinal axis extending between the distal and proximal ends. A cutter is located generally at the distal end of the catheter body for rotation generally about the longitudinal axis of the catheter body. The cutter has a proximal end portion, a distal end portion, and a longitudinal axis extending between the proximal and distal end portions. The cutter includes a cutting tip at the distal end portion of the cutter for removing tissue from the body lumen; and a deployment mechanism operatively connected to the cutter and the catheter body for selectively deploying and stowing the cutter. The deployment mechanism includes a camming element operatively connected to the cutter to allow for rotation of the cutter relative to the camming element, wherein the camming element is moveable axially with the cutter relative to the catheter body, and a cutter housing hingedly attached adjacent the distal end of the catheter body, the cutter housing being pivotable about a hinge axis generally transverse to the longitudinal axis of the catheter body and having a cutter window. The deployment mechanism is configured such that: proximal movement of the camming element relative to the catheter body and the cutter housing drives the cutter housing to pivot about the hinge axis so that the deployment mechanism opens, whereby the cutting tip extends through the cutter window and is exposed, and distal movement of the camming element relative to the catheter body and the cutter housing drives the cutter housing to pivot about the hinge axis so that the deployment mechanism closes, whereby the cutting tip is stowed in the cutter housing and unexposed.

In yet another embodiment, a catheter generally comprises an elongate catheter body configured for insertion into a body lumen of a subject. The catheter body has opposite distal and proximal ends, a longitudinal axis extending between the distal and proximal ends, and an interior tissue-transport passage extending along the longitudinal axis. A cutter is located generally at the distal end of the catheter body for rotation generally about the longitudinal axis of the catheter body. The cutter has a proximal end portion, a distal end portion, and a longitudinal axis extending between the proximal and distal end portions. The cutter includes an annular cutting tip at the distal end portion of the cutter for removing tissue from the body lumen, and a tissue passage defined by an interior surface of the cutter extending proximally from annular cutting tip, and having an inlet adjacent the annular cutting tip and an outlet extending through the cutter. A driveshaft is operatively connected to the proximal end portion of the cutter for selectively imparting rotation to the cutter relative to the catheter body. A cutter adaptor is operatively connected to the cutter and defines an internal passage connecting the tissue passage of the cutter with the interior tissue-transport passage of the catheter body. The cutter adaptor defines a shearing edge proximal of and adjacent to the outlet of the tissue passage. The cutter is rotatable relative to the shearing edge to cut tissue passing proximally into the internal passage through the outlet of the tissue passage.

In another aspect, a catheter generally comprises an elongate catheter body configured for insertion into a body lumen of a subject. The catheter body has opposite distal and proximal ends, a longitudinal axis extending between the distal and proximal ends, and an interior tissue-transport passage extending along the longitudinal axis. A driveshaft extends axially through the interior tissue-transport passage and is configured for rotational about its longitudinal axis. A cutter is located generally at the distal end of the catheter body for rotation generally about the longitudinal axis of the catheter body. The cutter has a proximal end portion, a distal end portion, and a central longitudinal axis extending between the proximal and distal end portions. The cutter includes an annular cutting tip at the distal end portion of the cutter for removing tissue from the body lumen. A tissue passage is defined by an interior surface of the cutter extending proximally from annular cutting tip, and having an inlet adjacent the annular cutting tip and an outlet extending through the cutter. A stem at the distal end portion is operatively connected to the driveshaft for selectively imparting rotation to the cutter about the central longitudinal axis of the catheter. The stem defines an eccentric camming portion that is radially offset from the central longitudinal axis of the cutter. A cutter adaptor defines an internal passage connecting the tissue passage of the cutter with the interior tissue-transport passage of the catheter body. The cutter adaptor includes an internal thread in the internal passage. The stem and the internal thread are configured such that the eccentric camming portion of the stem rides along the internal thread as the cutter is rotated by the driveshaft.

In yet another aspect, a catheter generally comprises an elongate catheter body configured for insertion into a body lumen of a subject. The catheter body has opposite distal and proximal ends, a longitudinal axis extending between the distal and proximal ends, and an interior tissue-transport passage extending along the longitudinal axis. A driveshaft extends axially through the interior tissue-transport passage and is configured for rotational about its longitudinal axis. A cutter is located generally at the distal end of the catheter body for rotation generally about the longitudinal axis of the catheter body. The cutter has a proximal end portion, a distal end portion, and a central longitudinal axis extending between the proximal and distal end portions. The cutter includes an annular cutting tip at the distal end portion of the cutter for removing tissue from the body lumen, and a tissue passage defined by an interior surface of the cutter extending proximally from annular cutting tip, and having an inlet adjacent the annular cutting tip and an outlet extending through the cutter. A guard is disposed immediately distal of the annular cutting tip of the cutter. The guard is configured to cover at least about one half of a circumferential portion of the annular cutting tip to inhibit tissue removed from the body lumen and disposed in the tissue passage from exiting the cutter distally through the annular cutting tip.

Other objects and features will be in part apparent and in part pointed out hereinafter.

DESCRIPTION OF THE DRAWINGS

FIG. 2 is similar FIG. 2A, except a cutter housing is removed to show hidden components;

FIG. 4B is similar to FIG. 4A, except the cutter housing is removed to show hidden components;

Corresponding reference characters indicate corresponding parts throughout the drawings.

DETAILED DESCRIPTION OF THE DRAWINGS

Figure 1:
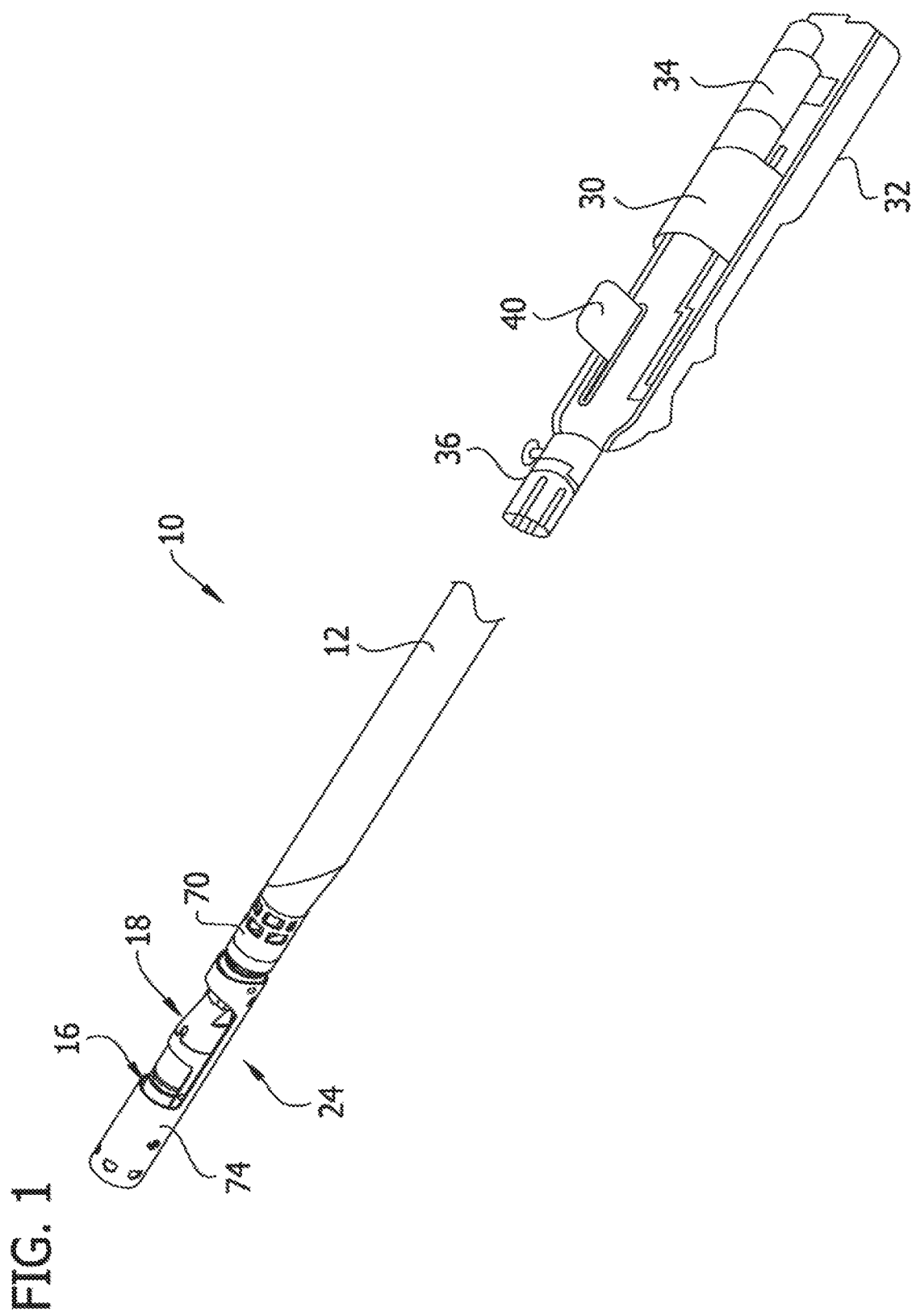
FIG. 1 is a fragmentary perspective of an embodiment of a tissue-removing catheter, including a removable handle attachable to a proximal end of the catheter.
Figure 2A:
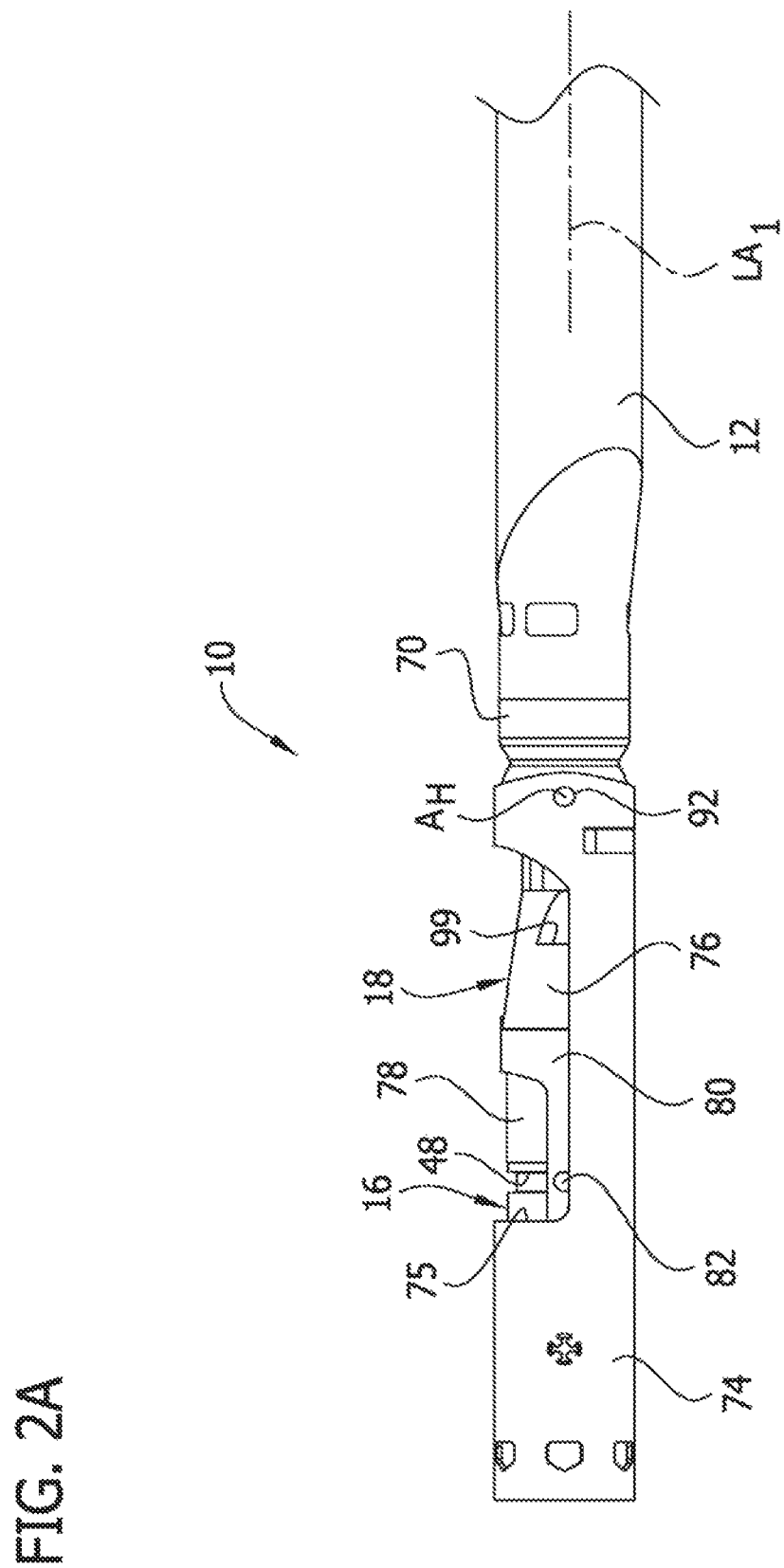
FIG. 2A is an enlarged fragmentary side elevation of a distal end portion of the tissue-removing catheter, with the tissue-removing catheter in a retracted position.

Referring now to the drawings, several embodiments of a tissue-removing catheter for removing tissue from a body lumen are disclosed. In particular, the illustrated catheter embodiments are suitable for removing tissue from a body lumen, and are particularly suitable for removing (i.e., excising) plaque tissue from a vessel (e.g., peripheral artery or peripheral vein). Features of the disclosed embodiments, however, may also be suitable for treating chronic total occlusion (CTO) of blood vessels, particularly peripheral arteries, and stenoses of other body lumens and other hyperplastic and neoplastic conditions in other body lumens, such as the ureter, the biliary duct, respiratory passages, the pancreatic duct, the lymphatic duct, and the like. Neoplastic cell growth will often occur as a result of a tumor surrounding and intruding into a body lumen. Removal of such material can thus be beneficial to maintain patency of the body lumen. While the remaining discussion is directed toward catheters for removing tissue from and penetrating occlusions in blood vessels (e.g., atheromatous or thrombotic occlusive material in an artery, or other occlusions in veins), it will be appreciated that the teachings of the present disclosure apply equally to other types of tissue-removing catheters, including, but not limited to, catheters for penetrating and/or removing tissue from a variety of occlusive, stenotic, or hyperplastic material in a variety of body lumens.

Figure 3:
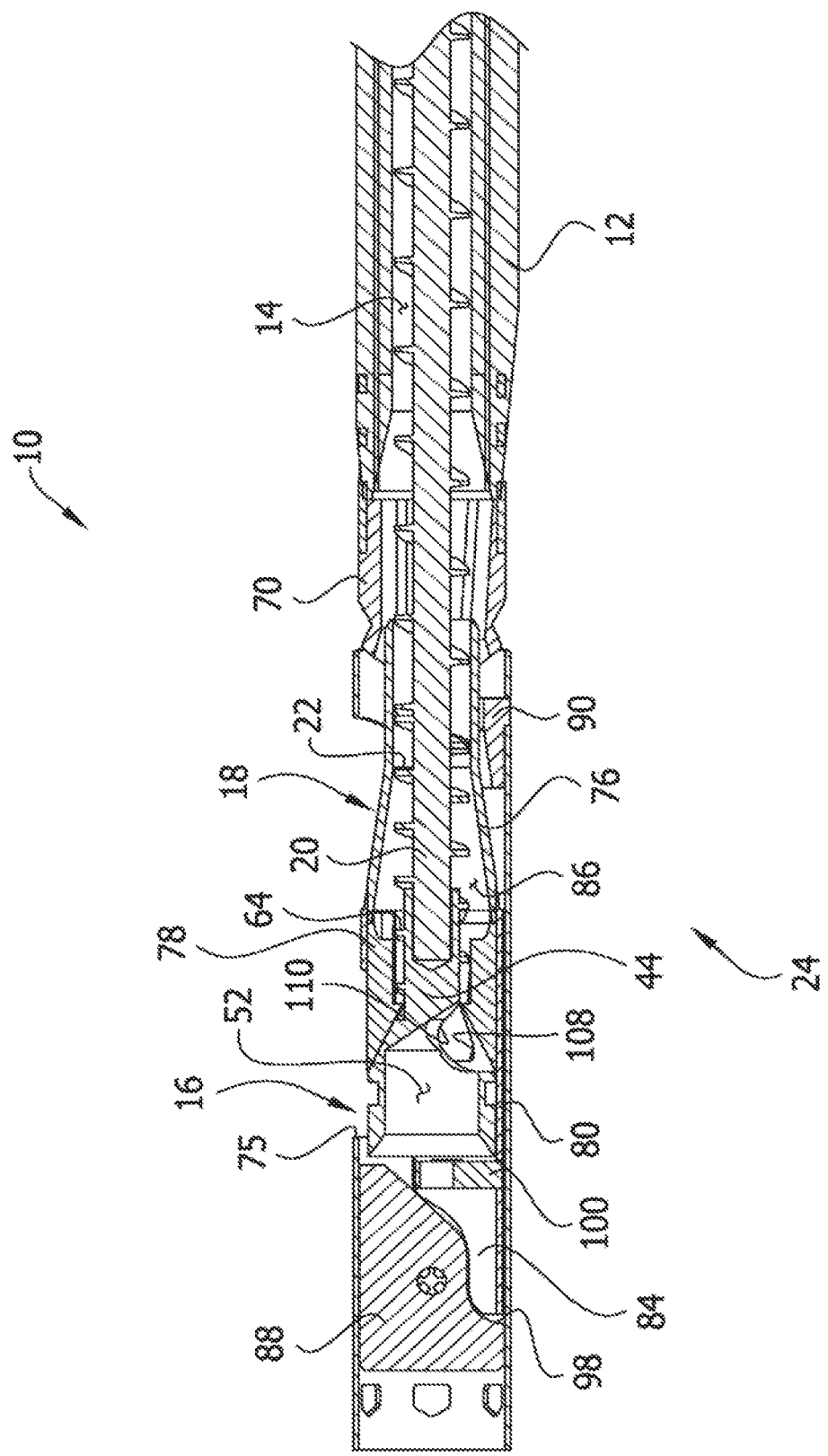
FIG. 3 is a longitudinal section of the distal end portion of the tissue-removing catheter of FIG. 2A.
Figure 4A:
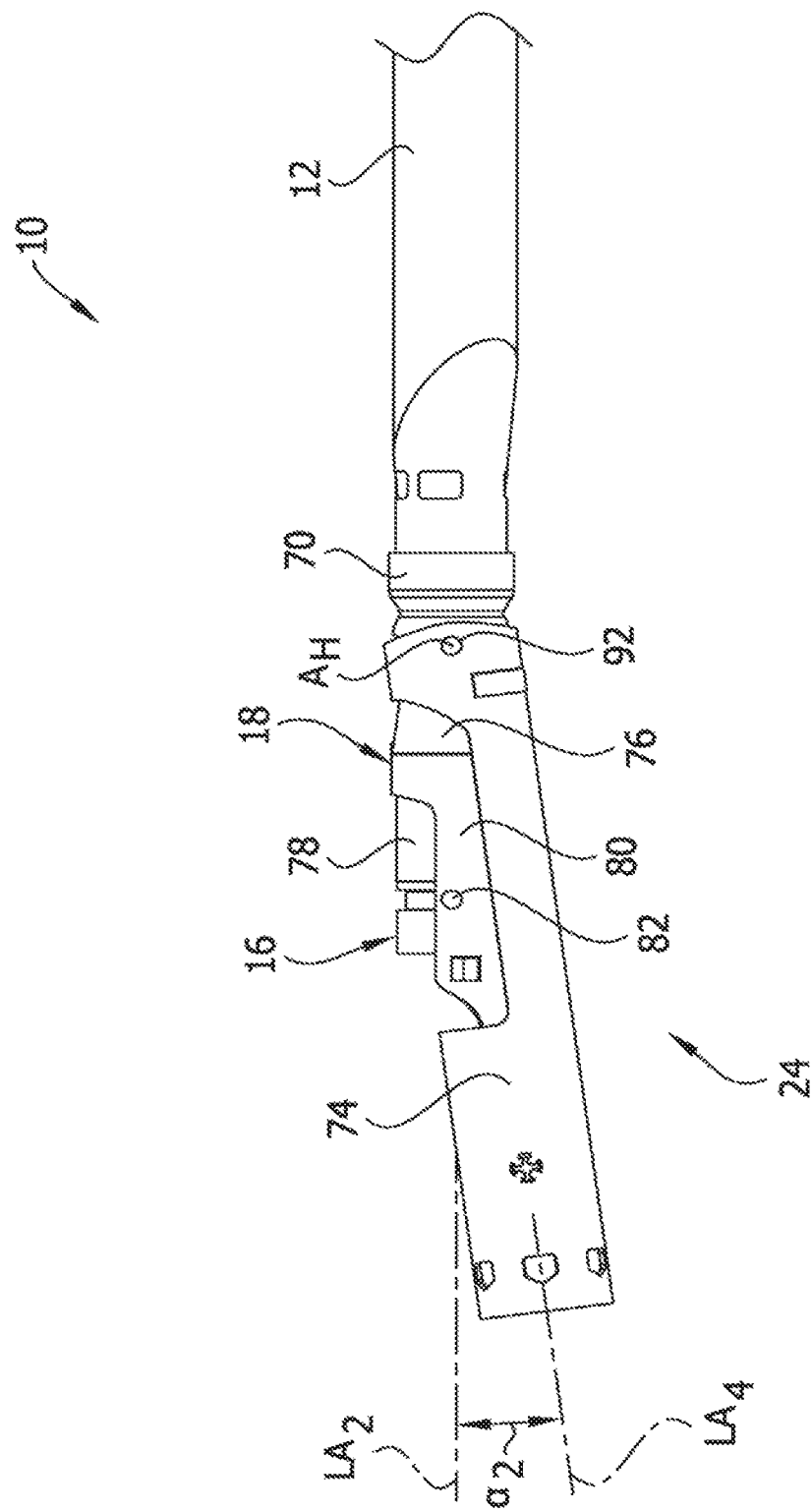
FIG. 4A is an enlarged side elevation of the distal end portion of the tissue-removing catheter, with the tissue-removing catheter in a deployed position.
Figure 5:
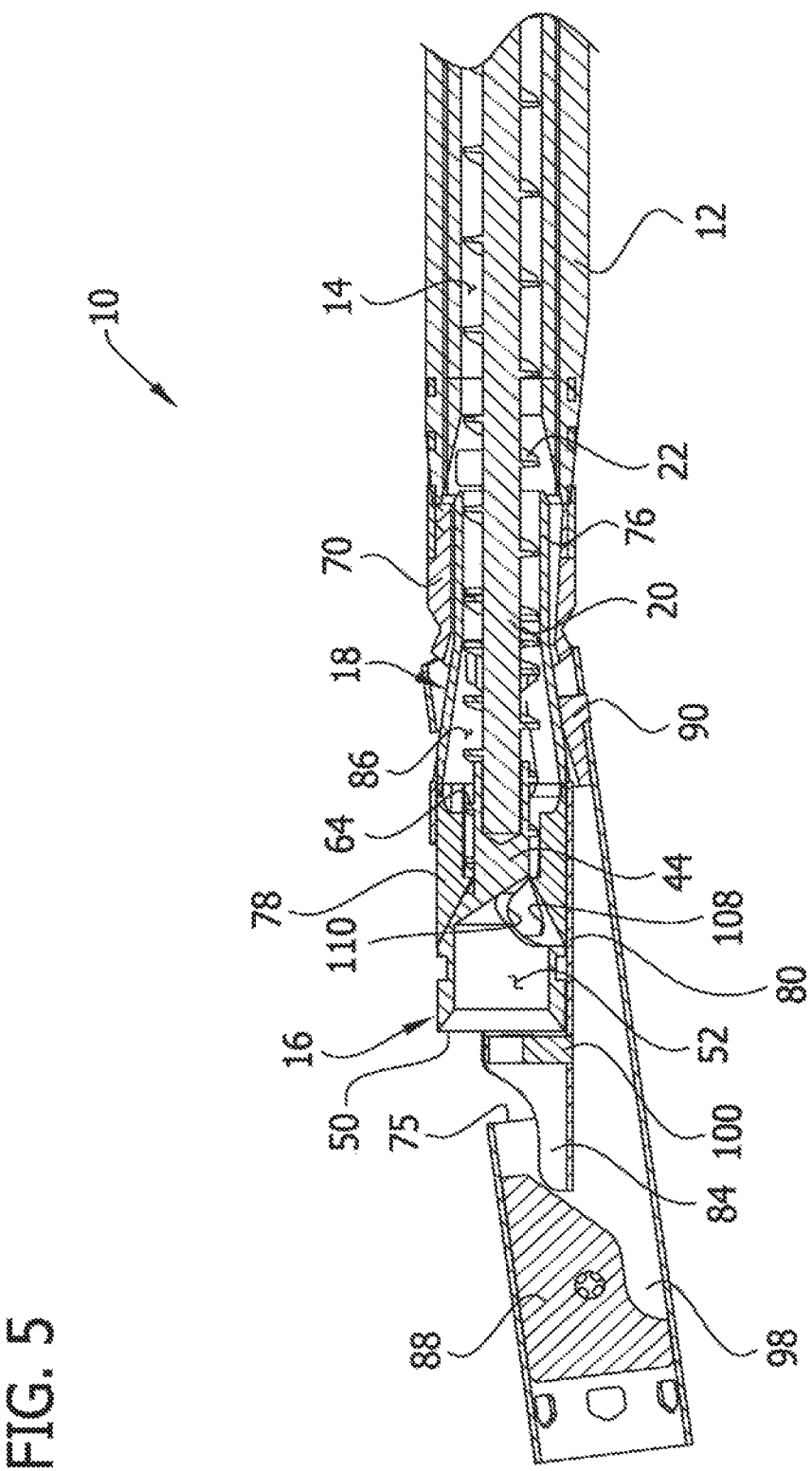
FIG. 5 is a longitudinal section of the distal end portion of the tissue-removing catheter of FIG. 4A.

Referring now to FIGS. 1-9, a first embodiment of a catheter, and more particularly, a tissue-removing catheter, is generally indicated by reference numeral 10. Briefly, the tissue-removing catheter 10 includes an elongate tubular catheter body 12 having opposite proximal and distal ends, a central longitudinal axis $LA_1$ (FIG. 2) extending between the distal and proximal ends, and an internal tissue-transport passage 14 (FIGS. 3 and 5) extending generally along the longitudinal axis of the body. Referring to FIGS. 2-5, a rotatable cutter, generally indicated at 16, is operatively connected to the distal end of the catheter body 12 for removing tissue from body lumen. In particular, in the illustrated embodiment the cutter 16 is operatively connected to a cutter adaptor, generally indicated at 18. A driveshaft 20 (FIGS. 3 and 5), which includes an external helical thread 22, drives rotation of the cutter 15 and also transports or moves removed tissue proximally within the tissue-transport passage 14 of the catheter body 12. A deployment mechanism, generally indicated at 24, configures the tissue-removing catheter 10 between a retracted position in which the cutter is not exposed for cutting (FIGS. 1, 2A and 3) and a deployed position in which the cutter is exposed for cutting (FIGS. 4A and 5). As explained in detail below, in the illustrated embodiment the cutter adaptor 14 functions as part of the deployment mechanism 24 and also constitutes, by virtue of an additional function, as a tissue shearing member to facilitate proximal transport of the removed tissue within the cutter adaptor.

Referring still to FIG. 1, the catheter body 12 is configured (e.g., sized and shaped) for intravascular introduction into the target artery, although as explained above, the catheter body may be configured for intraluminal introduction into other target body lumens other than a target artery. Although not illustrated, the catheter 10 may be configured for introduction of the catheter body 12 over a guidewire to a target site within the vasculature, in particular, the catheter 10 may be configured for "over-the-wire" introduction when a guidewire channel extends fully through the catheter body 12 or for "rapid exchange" introduction where the guidewire channel extends only through a distal portion of the catheter body. In other cases, it may be possible to provide a fixed or integral coil tip or guidewire tip on the distal portion of the catheter 10 or even dispense with the guidewire entirely. Moreover, a flexible, atraumatic distal tip (not shown) may be secured to the distal end of the illustrated catheter to facilitate insertion of the catheter. For convenience of illustration, guidewires will not be shown in any embodiment, but it should be appreciated that they can be incorporated into any of these embodiments.

The dimensions and other physical characteristics of the catheter body 12 may vary depending on the artery for other body lumen) of the subject which is to be accessed. The catheter body 12 is generally flexible and may in one embodiment have a length in the range from 50 cm to 200 cm and an outer diameter in the range from 1 French to 12 French (0.33 mm: 1 French), such as from 3 French to 9 French. The catheter body 12 may be composed of an organic polymer which is fabricated by extrusion techniques. Suitable polymers include polyvinylchloride, polyurethanes, polyesters, polytetrafluoroethylenes (PTFE), silicone rubbers, natural rubbers, and the like. Optionally, the catheter body 12 may be reinforced with a braid, helical wires, coils, axial filaments, or the like, in order to increase rotational strength, column strength, toughness, pushability, and the like. For example, the catheter body 12 may include a torque tube, as is generally known in the art. The outer diameter of the catheter body 12 can be modified by heat expansion and shrinkage using conventional techniques. It will be appreciated that the construction and dimensions of the catheter body may be other than described without departing from the scope of the present invention.

The catheter body 12 of the present embodiment may include an urging mechanism (not shown) to urge the cutter into engagement with the body lumen wall during treatment. For example, the urging mechanism may comprise a portion of the catheter body adjacent to and proximal of the cutter that is biased to (e.g., permanently deformed in) a double-bent or double-curved shape to urge the cutter toward a wall of a body lumen to enhance treatment. A suitable urging mechanism is disclosed in U.S. Pat. No. 7,708,749, the relevant teaching of which is hereby incorporated by reference. In other embodiments, the urging mechanism may take many other suitable forms. The catheter may not include an urging mechanism without departing from the scope of the present invention.

Referring to FIGS. 3 and 5, as set forth above, the catheter 10 includes the rotatable cutter 16 and the driveshaft 20 for imparting rotation of the cutter. The driveshaft 20 extends along the tissue-transport passage 14 of the catheter body 12 and is selectively movable axially therein (i.e., generally along the longitudinal axis LA of the body) to actuate the deployment mechanism 24, as explained in detail below. A distal end portion of the driveshaft 20 is operatively connected to the rotatable cutter 15 for selectively driving rotation of the cutter generally about the longitudinal axis $LA_1$ of the catheter body 12. In the illustrated embodiment) the distal end portion of the driveshaft 20 is fixedly secured to the cutter 16. The shank of the driveshaft 20 (i.e., the part of the driveshaft not including the thread 22) is generally flexible and may be formed from one or more coils (e.g., stainless steel coil(s)), or a torque tube (e.g., a polyimide tube with a layer of braided stainless steel wire embedded therein). The body of the driveshaft 20 may have a very high torsional stiffness and sufficient tensile strength, but which is generally laterally flexible. Depending upon the desired torque transmission, diameter and flexibility, any of a variety of other materials and constructions may also be used.

In the illustrated embodiment, the helical thread 22 on the exterior of the driveshaft 20 extends along the length of the driveshaft and functions as a transport mechanism for transporting removed tissue proximally within the tissue-transport passage 14 of the catheter body 12. Accordingly, the threaded driveshaft 20 functions as an auger or a screw conveyer, whereby rotation of the driveshaft imparts rotation of the helical thread 22, which moves removed tissue proximally within the catheter body 12. In the illustrated embodiment, the thread 22 is a right-handed thread as viewed from the proximal end of the driveshaft 20), such that rotation of the driveshaft 20 clockwise (as viewed from the proximal end of the driveshaft 20) transports the tissue proximally. The tissue transport passage 14 and driveshaft thread 22 may extend back to the proximal end portion of the catheter body 12 and may empty into a tissue receptacle (not shown). The tissue transport passage 12 and driveshaft thread 22 may stop short of the proximal end portion of the catheter body 12. The thread 22 may be formed on the driveshaft 20 in a suitable manner.

In one example, shown in FIGS. 3 and 5, the cross-sectional dimension (e.g., inner diameter) of the tissue-transport passage 14 is slightly greater than the major diameter of the exterior thread 22 on the driveshaft 20 so that there is a small radial gap (or play) between the exterior thread on the driveshaft and interior surface defining the tissue-transport passage 14. In this example, the radial gap is such so as not to inhibit or impede rotation and axial movement of the driveshaft 20 in tissue-transport passage 14, and at the same time, substantially inhibit tissue from passing between the thread 22 on the driveshaft 20 and the interior surface defining the tissue transport passage. For example, the diameter of the tissue-transport passage 14 may be from about 0.001 in (0.025 mm) to about 0.020 in (0.508 mm) greater than the major diameter of the exterior thread 22. It is understood that other types of transport mechanisms (e.g., aspiration devices, or other types of auger transport mechanisms) may be used with the catheter 10, in lieu of the helical thread 22 on the driveshaft 20. It is also understood that the transport mechanism may be omitted without departing from the scope of the present invention.

For example, a chamber may be provided proximal or distal the cutter 16 to store removed tissue.

Referring to FIG. 1, the proximal end of the driveshaft 20 is operably connected to a cutter motor 30 (broadly, a cutter driver) to impart rotation of the driveshaft 20 relative to catheter body 12. In one example, the cutter motor 30 is disposed within a handle 32 (shown with a cover removed in FIG. 1) that is releasably connectable to the proximal end of the catheter 10. For example, in addition to the cutter motor 30, the handle 32 may house a power source 34 (e.g., batteries) for the cutter motor 30, a microswitch (not shown) for activating cutter motor, and a catheter connector 36 for operatively connecting the motor to the proximal end portion of the driveshaft 20. In some embodiments, the cutter motor 30 can rotate the driveshaft 20 between 1,000 rpm and 10,000 rpm or more, if desired. As explained in more detail below, the handle 32 may include one or more input devices, such as lever 40, which controls the major operations of the catheter 10, such as axial movement of the driveshaft 20 to actuate the deployment mechanism 24, and rotation of the driveshaft 20 and the cutter 16 via the cutter driver 30. It is understood that the driveshaft 20 may be driven in other ways without departing from the scope of the present invention.

Figure 7:
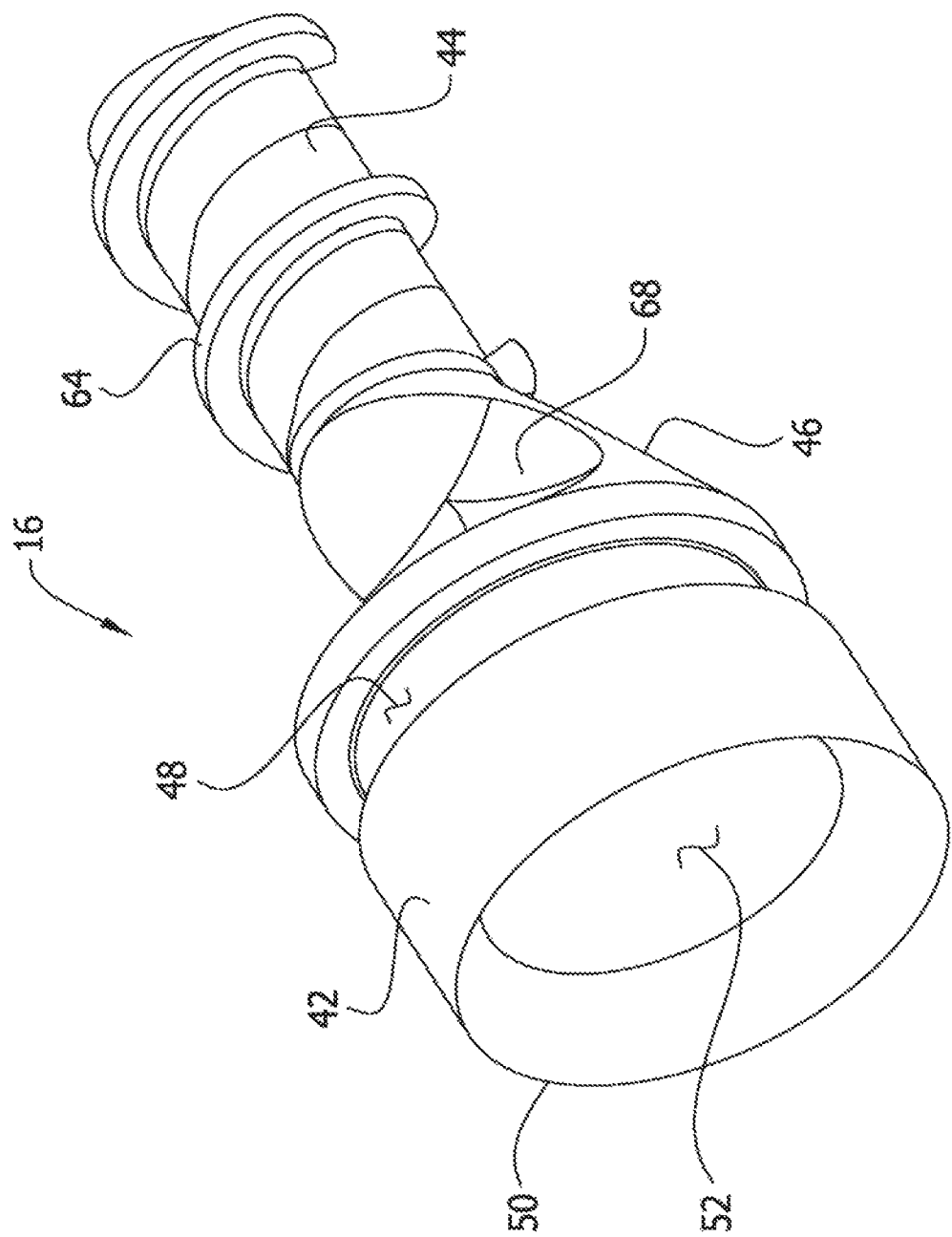
FIG. 7 is an enlarged, front perspective of the cutter of the tissue-removing catheter.
Figure 8:
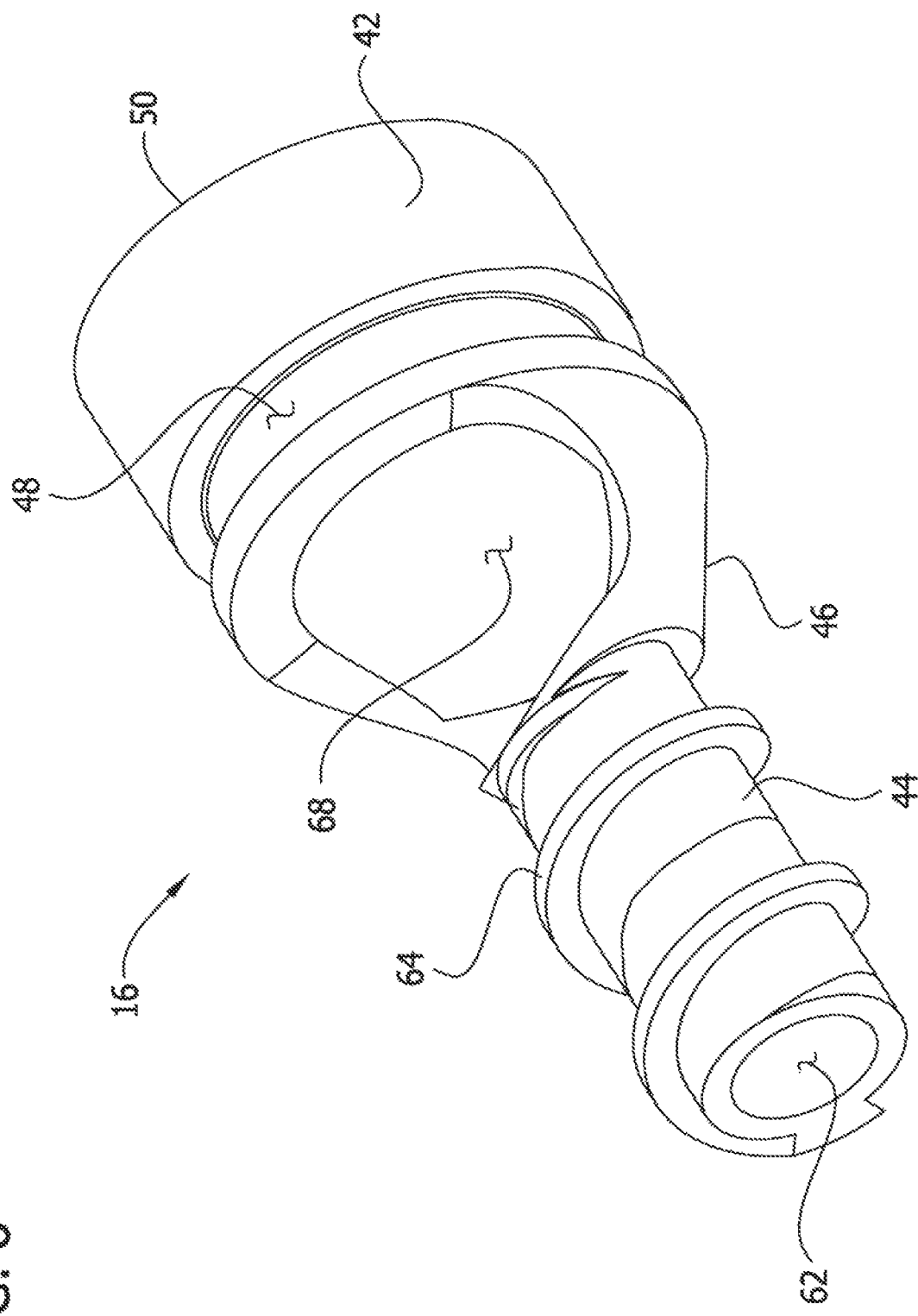
FIG. 8 is an enlarged, rear perspective of the cutter of the tissue-removing catheter.
Figure 9:
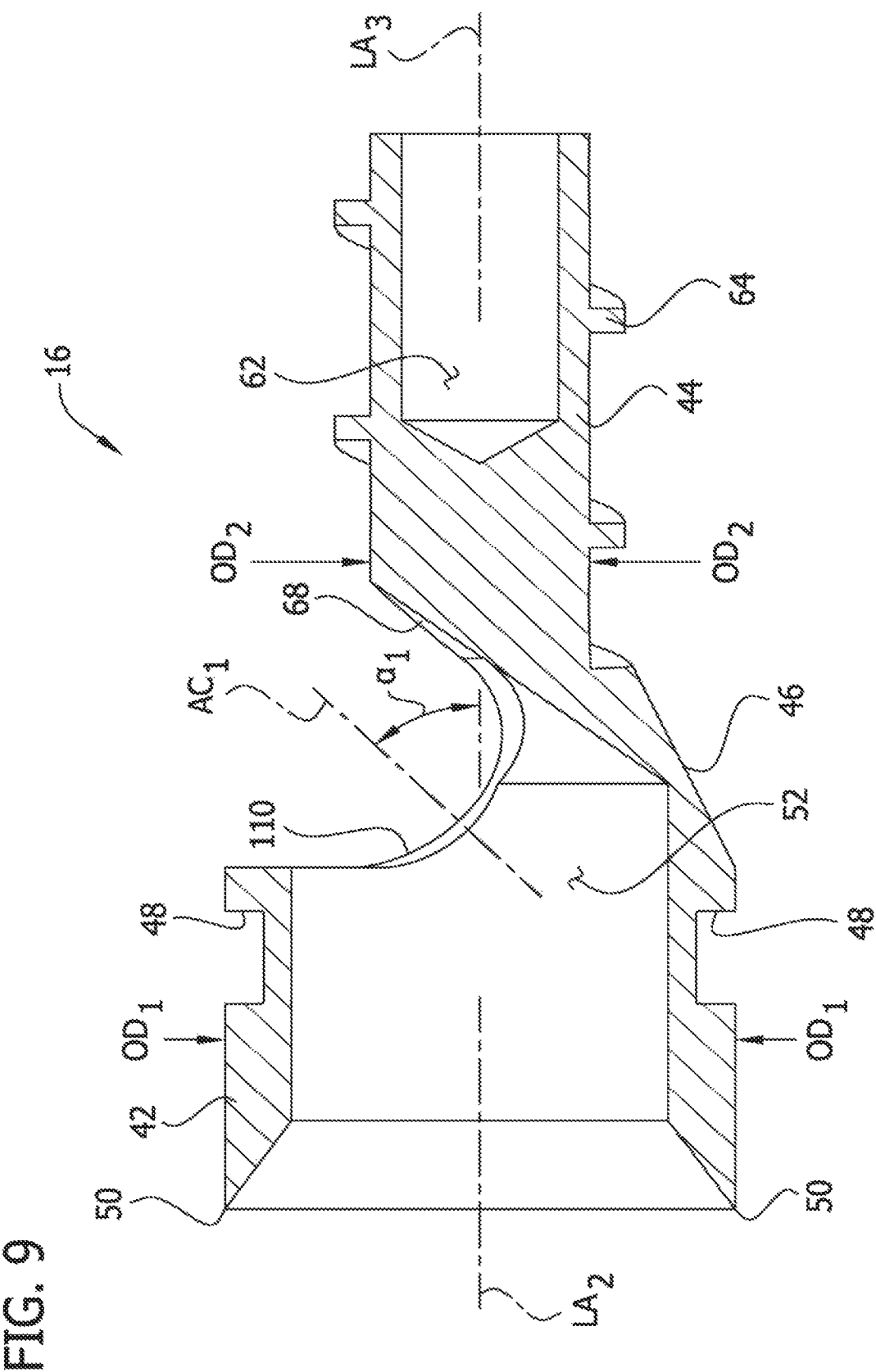
FIG. 9 is an enlarged, longitudinal section of the cutter.

As seen best in FIGS. 7-9, the rotatable cutter 16 has opposite proximal and distal ends and a longitudinal axis $LA_2$ extending therebetween. The cutter 16 has a generally cylindrical distal cutting portion 42, a proximal stem 44 (broadly, a driveshaft-connection portion) for connecting the cutter to the driveshaft 24, and a transitional portion 46 intermediate the distal cutting portion and the stem. The distal cutting portion 42 has an outer cross-sectional dimension $OD_1$ (e.g., an outer diameter) that is greater than an outer cross-sectional dimension $OD_2$ (e.g., an outer diameter) of the stem 44, and the exterior of the transitional portion 46 tapers (e.g., necks down) longitudinally from the distal cutting portion to the stem. For reasons explained below, the exterior surface of the distal cutting portion 42 has a circumferential groove 48 formed therein. The cutter 16 may be formed as a single, one-piece construction, or may be formed from separate components secured to one another in a suitable manner, such as welding, soldering, adhesives, mechanical interference fit, threaded engagement and the like. As a non-limiting example, the cutter 16 may be comprised of steel, tungsten carbide, tungsten carbide cobalt, tungsten carbide molybdenum, silicon carbide, silicon nitride, ceramic, amorphous metals or other materials and may be manufactured by methods including turning, grinding, sintering, electro-discharge machining (EDM), laser cutting, heat treating, precipitation hardening, casting or other methods.

Referring still to FIGS. 7-9, the distal cutting portion 42 of the cutter 16 includes an annular cutting tip 50 at the distal end thereof, and an axial cavity 52, defined by an interior surface of the cutter 16, extending from the cutting tip toward the stem 44 of the cutter. In one non-limiting example, the annular cutting tip 50 is beveled from an exterior surface of the cutter toward the interior surface to define the sharp, distal cutting edge. The beveled, annular cutting tip 50 creates a "negative angle of attack." The cutting tip 50 may be formed separately from the distal cutting portion 42 of cutter 16 and attached thereto, or the cutting tip may be formed integrally with the distal cutting portion of cutter. In the embodiment illustrated in FIGS. 7-9, the annular cutting tip 50 has a generally smooth surface. The cutting tip may be of other configurations without departing from the scope of the present invention. For example, other configurations of the cutting tip are disclosed below regarding FIGS. 10-16.

The stem 44 connects the cutter to the distal end of the driveshaft 20 such that rotation of the driveshaft imparts rotation of the cutter about its longitudinal axis $LA_2$ (i.e., the rotational axis of the cutter is coincident with the central longitudinal axis of the cutter). In the illustrated embodiment, and as shown in FIG. 9, a central longitudinal axis $LA_3$ of the stem 44 is coincident with the central longitudinal axis $LA_2$ of the cutter 116. The stem 44 defines a bore 62, having a central axis coincident with the central longitudinal axis of the stem, in which the distal end of the driveshaft 20 is secured. For example, the distal end of the driveshaft 20 may be secured in the bore 62 by soldering, welding, adhesive, press-fit interference, crimping, or in other ways. In the present illustrated embodiment, the stem 44 includes a helical, exterior thread 64 running along the length of the stem to further facilitate proximal transport of removed tissue, as explained in more detail below. In the illustrated embodiment (shown best in FIGS. 3 and 5), the exterior thread 64 on the stem 44 is aligned (or mates) with the thread 22 on the driveshaft 20 to form a substantially continuous thread extending from the stem along the driveshaft, in one example, the pitch of the stem thread 64 is the same as the pitch of the driveshaft thread 22, although the pitches may be different, in another embodiment, such as shown in FIGS. 10-13, the stem 44 may be free from an exterior thread.

As set forth above, the tissue removed from the body lumen by the cutting tip 50 passes proximally through the cutter 16, toward the tissue-transport passage 14 of the catheter body 12. In the illustrated embodiment, the cutter 16 has an eccentric opening 68 in communication with the axial cavity 52 to allow removed tissue to pass through the cutter. Together, the eccentric opening 68 and the axial cavity 53 define a tissue passage extending through the cutter 16. Thus, as can be seen from FIG. 5, as the tissue is being removed, it enters the axial cavity 52, and then passes through the eccentric opening 68 and into the cutter adaptor 18, where it can be picked up by the stem thread 64 and/or the driveshaft thread 22 (or other transport mechanism), and transported proximally within tissue-transport passage 14. Referring to FIG. 9, the eccentric opening 68 in the cutter 16 is offset with respect to the longitudinal axis $LA_2$ (and rotational axis) of the cutter. The eccentric opening 68 is shaped such that when viewed from the distal end of the cutter 16 looking proximally, the eccentric opening extends around the longitudinal axis $LA_2$ in an arc and does not intersect the longitudinal axis of the cutter. In the illustrated embodiment (see best in FIGS. 7-9), the eccentric opening 68 extends through the tapered transitional portion 46 of the cutter 16, such that the eccentric opening (as defined by an axis $AC_1$ that is parallel to the interior surface of the transitional portion 46) extends at an angle $\alpha_1$ that is neither coincident nor parallel with the longitudinal axis $LA_2$ (and rotational axis of the cutter. As a non-limiting example, the offset angle $\alpha_1$ may measure from about 15 degrees to about 60 degrees, and in one example, about 45 degrees, from the longitudinal axis $LA_2$ (and rotational axis) of the cutter 15 it is understood that the cutter 16 may be of other configurations in other embodiments of the catheter without departing from the scope of the present invention.

Referring to FIGS. 10-13, another embodiment of the cutter is indicated at reference numeral 16'. This cutter 16' is similar to cutter 16, and like components are indicated by corresponding reference numeral plus a prime symbol, in this embodiment, the beveled, annular cutting tip 50' may include one or more raised elements 56 (e.g., breakers). In the illustrated embodiment, four raised elements 56 are formed on the beveled, annular cutting tip 50, although in other embodiments more than four or less than four raised elements may be present. During removal of tissue from the target body lumen, the raised elements 56 produce a hammer-like impact against the tissue to be removed as the cutter 16' is rotated. In the case where the tissue to be removed has brittle characteristics (e.g., has become calcified), the tissue will be crushed into smaller particles thereby facilitating its removal. Repeated rotation of cutter 16 will produce repeated hammer-like blows of the cutter raised elements 56 against the tissue to be removed. The raised elements 56 are disclosed in U.S. patent application Ser. No. 12/958,488, filed Dec. 2, 2010, the relevant teachings of which relating to the raised elements disclosed thereon are incorporated by reference herein. The stem 44' of the present cutter 16 is also not threaded, unlike the stem 44 of the previous cutter 16. However, the cutter 16' could be provided with threads.

Figure 14:
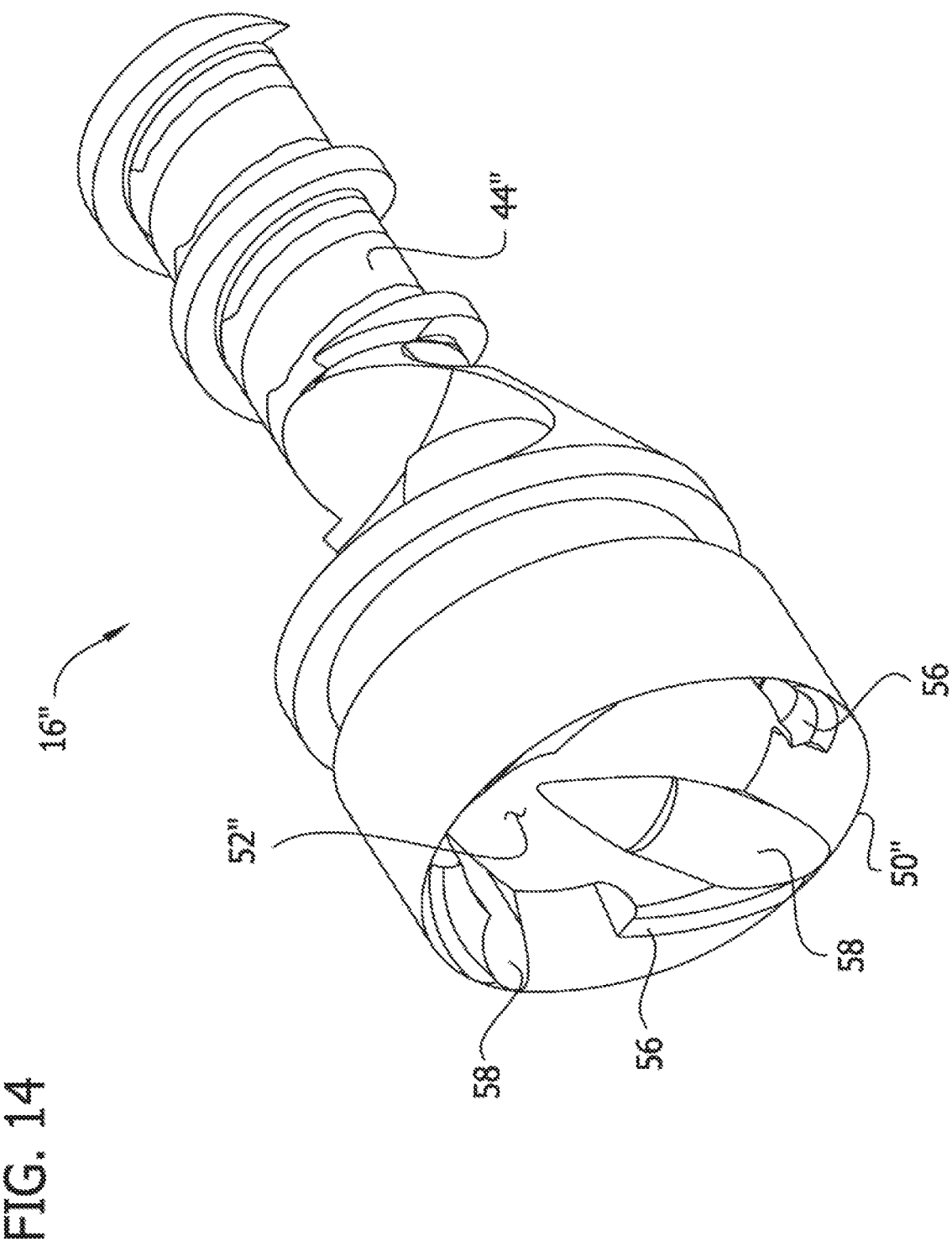
FIG. 14 is a front perspective of a third embodiment of a cutter for the tissue-removing catheter of FIG. 1.
Figure 15:
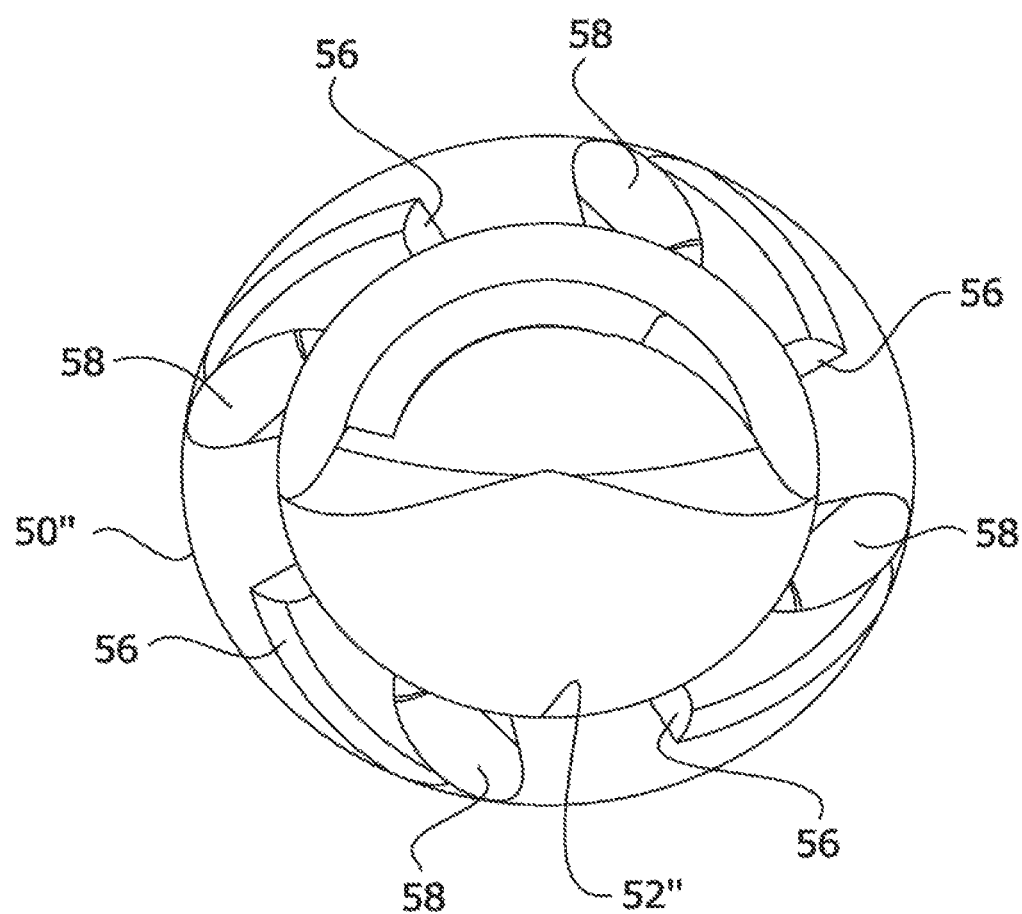
FIG. 15 is a front elevation of the cutter of FIG. 14.
Figure 16:
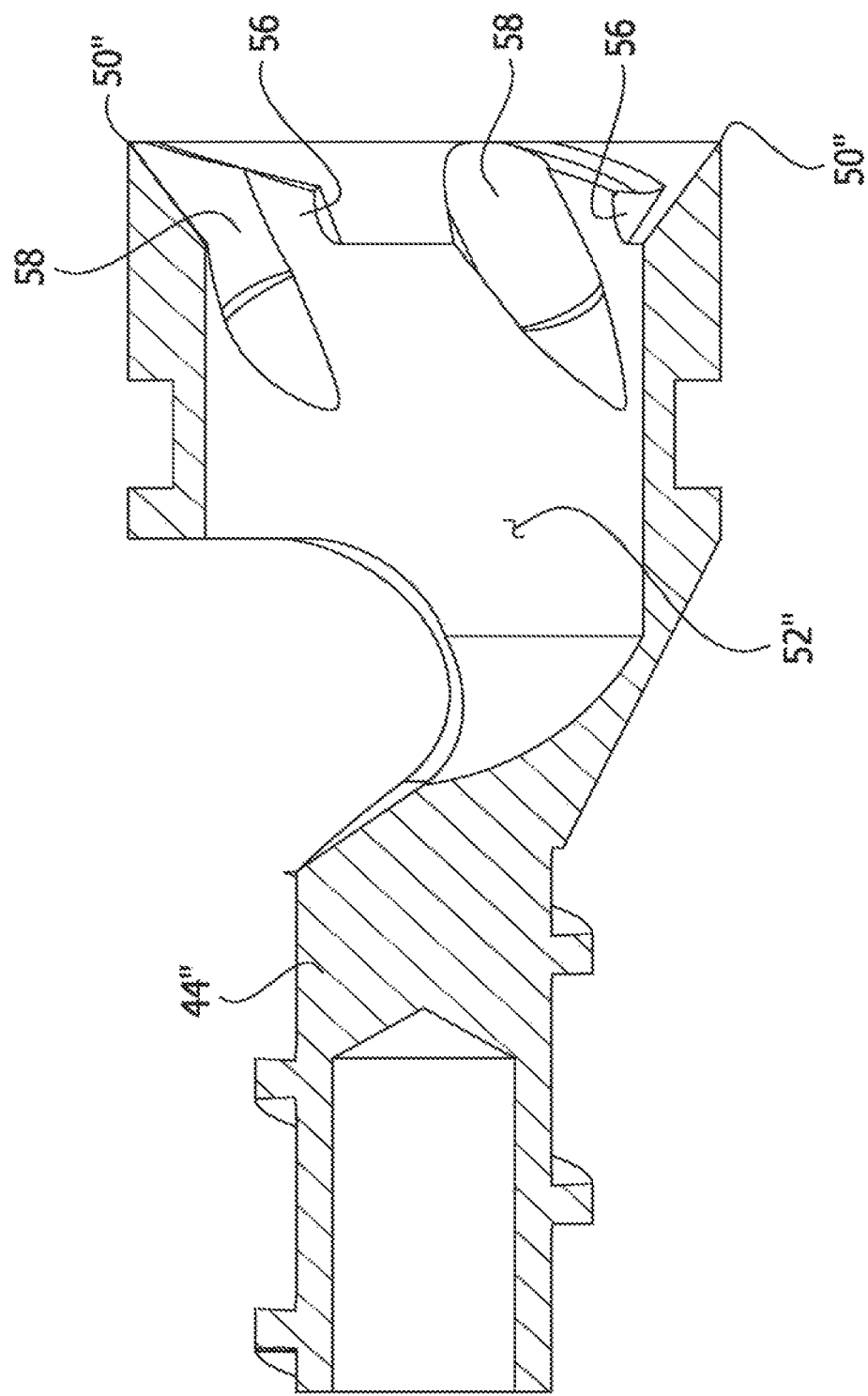
FIG. 16 is a longitudinal section of the cutter of FIG. 14.

Referring to FIGS. 14-16, another embodiment of the cutter is indicated at reference numeral 16". This cutter 16" is similar to cutter 16, and like components are indicated by corresponding reference numeral plus a double-prime symbol, in this embodiment, the annular cutting tip 50" includes one or more flutes 58 (i.e., spiral grooves) extending from adjacent the cutting tip to the interior surface defining the axial cavity 52". In the illustrated embodiment, the annular cutting tip 50' also includes the raised elements 56, disclosed above with respect to FIGS. 10-13, although the raised elements may be omitted in another embodiment. The flutes 58 are shaped and arranged to drive tissue proximally into the axial cavity 52" as the tissue is removed from the body lumen. The stem 44" is also threaded, like the stem 44 of the cutter 16.

As set forth above, the catheter 10 includes the deployment mechanism 24 for configuring the cutter 16 between the retracted position (FIGS. 1-3) and the deployed position (FIGS. 4A, 46 and 5). The deployment mechanism 24 is connected to a deployment adaptor 70 at the distal end of the catheter body 12. For purposes of the disclosure, the deployment adaptor 70 is considered part of the catheter body 12, and in particular, part of the distal end of the catheter body. In the illustrated embodiment, the deployment mechanism 24 includes a cutter housing 74, defining a cutter window 75, hingedly attached to the deployment adaptor 70 at the distal end portion of the catheter body 12.

The cutter adaptor 18 is axially (i.e., proximally and distally) moveable relative to the cutter housing 74, whereby proximal movement of the cutter adaptor drives the cutter housing to pivot about its hinge axis $A_H$ to open the deployment mechanism 24 and expose the cutting tip 50 through the cutter window 75 (FIG. 5), and distal movement of the cutter adaptor drives the cotter housing to pivot about its hinge axis to close the deployment mechanism so that cutting tip is retracted in the cutter housing (FIGS. 2 and 3). The cutter adaptor 18 is axially moveable relative to the cutter housing 74 (and the catheter body 12) by axially moving the driveshaft 20, which imparts axial movement to the cutter 16. Accordingly, the cutter adaptor 18 moves axially with the cutter 16, which is conjointly moveable by the driveshaft 20. In one embodiment, the driveshaft 20 is axially moveable relative to the catheter body 12 by actuating the lever 40 on the handle 32, which may also actuate the motor 30 to drive rotation of the driveshaft and the cutter 15.

Referring to FIGS. 2-6B, in the illustrated embodiment, the cutter adaptor 18 includes a proximal tube piece 76 and a distal tube piece 78 (together defining an adaptor tube or adaptor tube assembly) connected to a cradle-shaped, rotational bearing member 30 that receives and supports the cutter 16. The bearing member 80 is received in the cutter housing 74 and is axially slideable therein, in particular, in the illustrated embodiment, the bearing member 80 has an exterior surface having an arcuate cross-sectional shape that is generally complementary to the exterior arcuate cross-sectional shape of the cutter housing 74, such that the bearing member nests in the cutter housing. In the illustrated embodiment, the components of the cutter adaptor 18 are formed as separate components and secured to one another by in a suitable fashion, such as by adhesive, welding, fasteners, or the like. Alternatively, selective components (including all of the components) may be formed integrally as a single, one-piece component. For example, the tube pieces 76, 78 may be formed as a single, one-piece component. The respective components of the cutter adaptor 18, including the distal tube piece 78, the proximal tube piece 76, the bearing member 80, and the cutter housing 74 may be formed from stainless steel or other biocompatible material.

The rotational bearing member 80 is configured to allow rotator of the cutter 16 generally about the longitudinal axis $LA_1$ of the catheter body 12 relative to the cutter adaptor 18, while substantially inhibiting axial movement of the cutter relative to the cutter adaptor, such that the cutter adaptor moves axially with the cutter. The rotational bearing member 80 also retains the cutter 16 is proper position relative to the cutter adaptor 18 as the cutter is rotated by the driveshaft 20. To this end, the bearing member 80 has an internal support surface having an arcuate cross-sectional shape that is generally complementary to the exterior arcuate cross-sectional shape of the distal tube piece 78 and the annular cutting tip 50 of the cutter 16 for supporting the cutter and the distal tube piece. In the illustrated embodiment, the bearing member 80 includes pins 82 received in the circumferential groove 48 in the exterior surface of the cutter 16. The cutter adaptor 18, more specifically, the rotational bearing member 80, includes a tongue 84 extending distally relative to the cutting tip 50. As explained below, the tongue 84 interacts with a closing ramp follower 88 of the cutter housing 74 when the cutter adaptor 18 is moved distally to facilitate retracting the cutter 16 within the cutter housing. The rotational bearing member 80 may be of other configurations and types without departing from the scope of the present invention.

Figure 21:
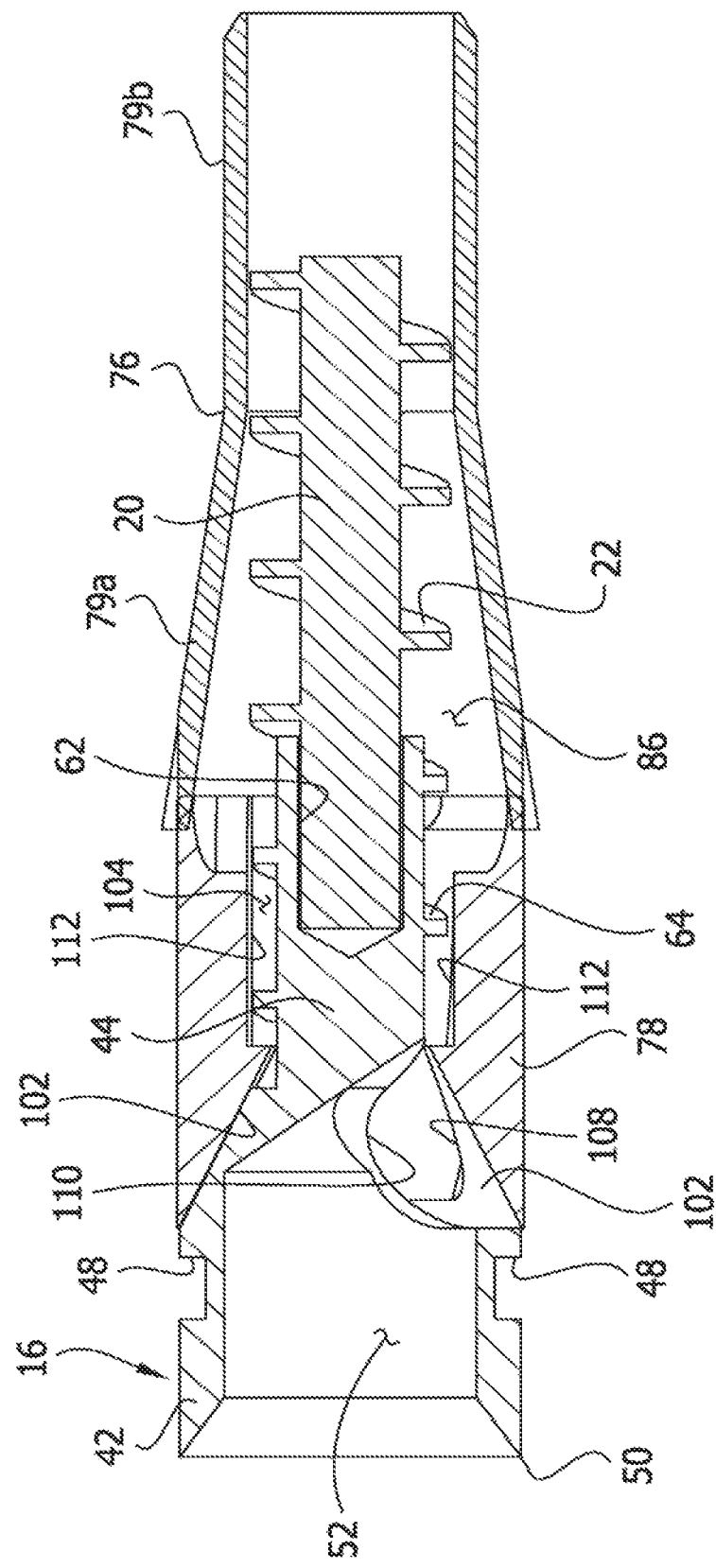
FIG. 21 is an enlarged longitudinal section similar to FIG. 3 with a cutter housing and a catheter body removed therefrom, a driveshaft being shown broken for illustrative purposes.
Figure 22:
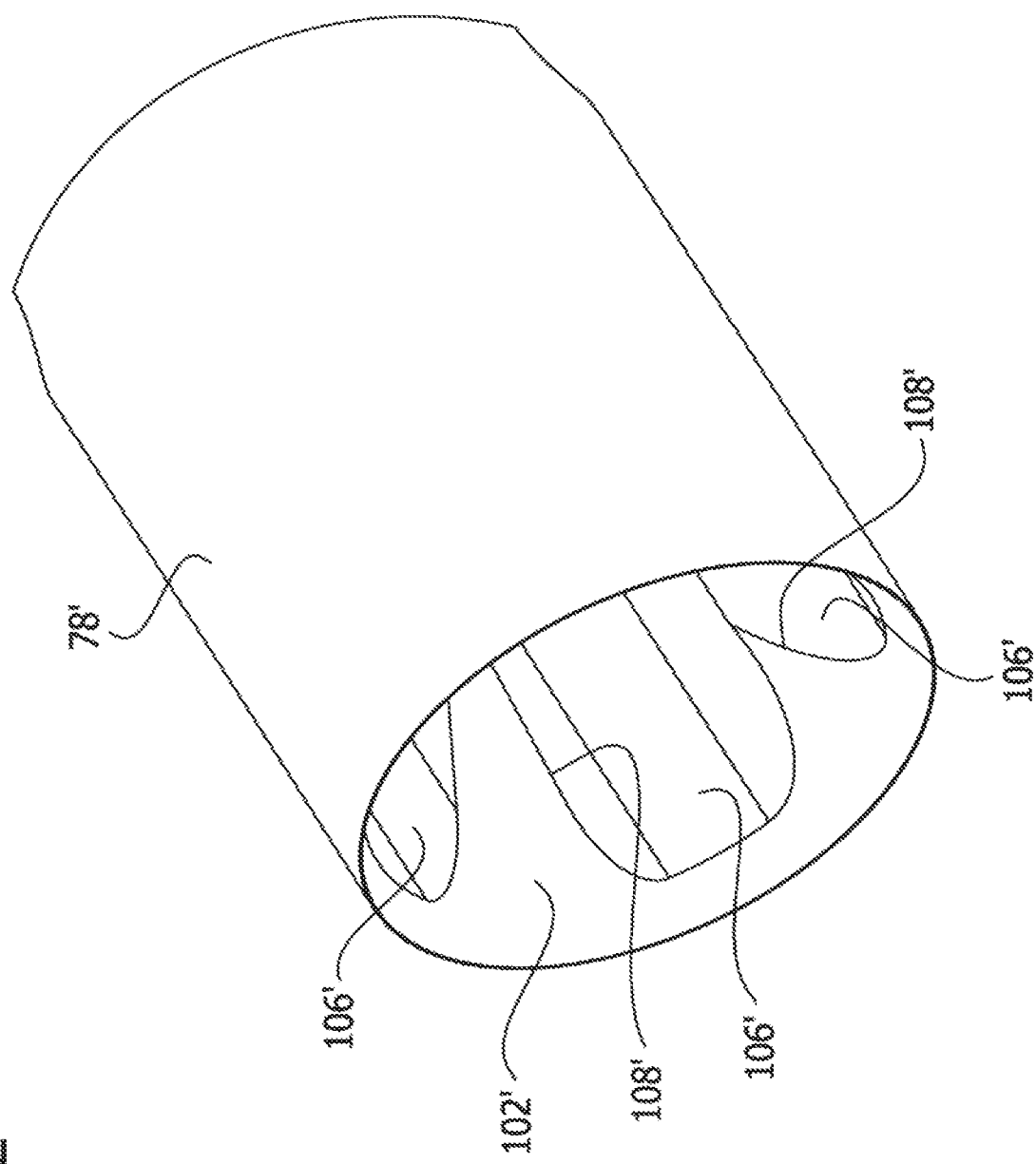
FIG. 22 is an front perspective of a second embodiment of a distal tube piece for the tissue-removing catheter of FIG. 1.
Figure 23:
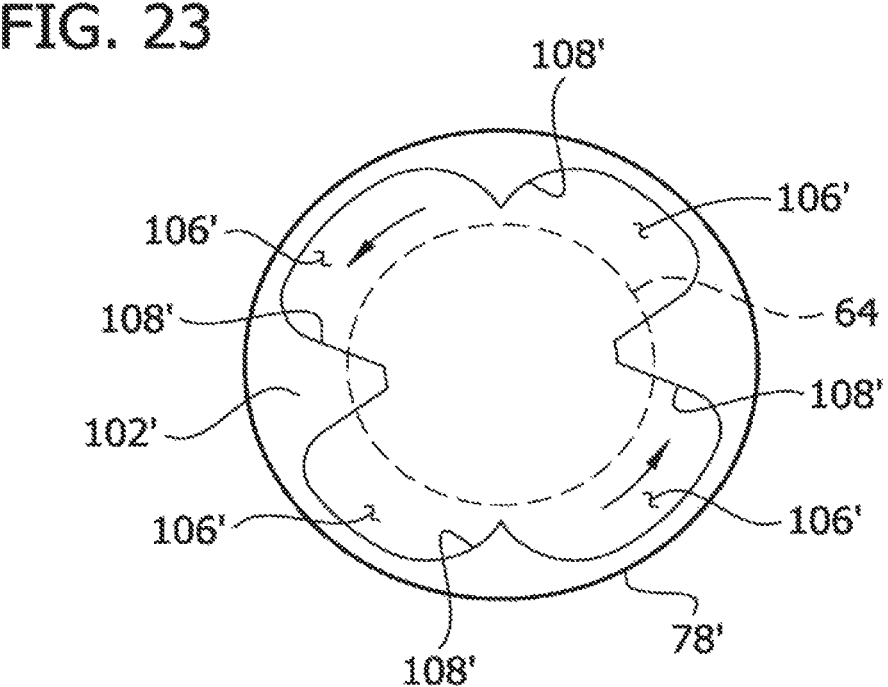
FIG. 23 is a front elevation of the distal tube piece of FIG. 22, with an external thread of a cutter stem shown in broken lines.
Figure 24:
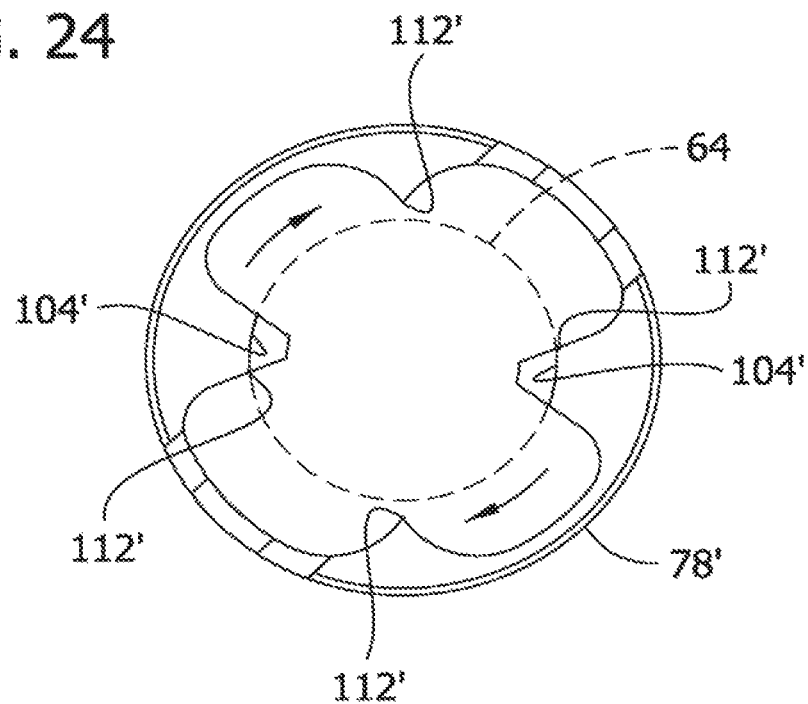
FIG. 24 is a rear elevation of the distal tube piece of FIG. 22, with an external thread of a cutter stem shown in broken lines.

Referring to FIGS. 3-5 and 21, the proximal and distal tube pieces 76, 78, respectively, together define an internal passage 86 of the cutter adaptor 18 in which a portion of the cutter 16 (e.g., the transitional and proximal portions 46, 44 of the cutter) and a portion of the driveshaft 20 (e.g., the distal end portion of the driveshaft) are received. As shown in FIG. 21, the exterior of the proximal tube piece 76 has a transitional portion 79a tapering proximally from the rotational bearing member 80, and proximal portion 79b that is received in the tissue-transport passage 14 at the distal end portion of the catheter body 12 to connect the internal passage 86 of the adaptor tube assembly with the tissue-transport passage 14. As explained below, the exterior of the proximal tube piece 76 interacts with an opening ramp follower 90 of the cutter housing 74 when the cutter adaptor 18 is moved proximally to facilitate opening of the deployment mechanism 24. The opening ramp follower 90 and closing ramp follower 88 remain in operative contact with the caroming element as described below) in all relative positions of the cutter housing and camming element.

Figure 6A:
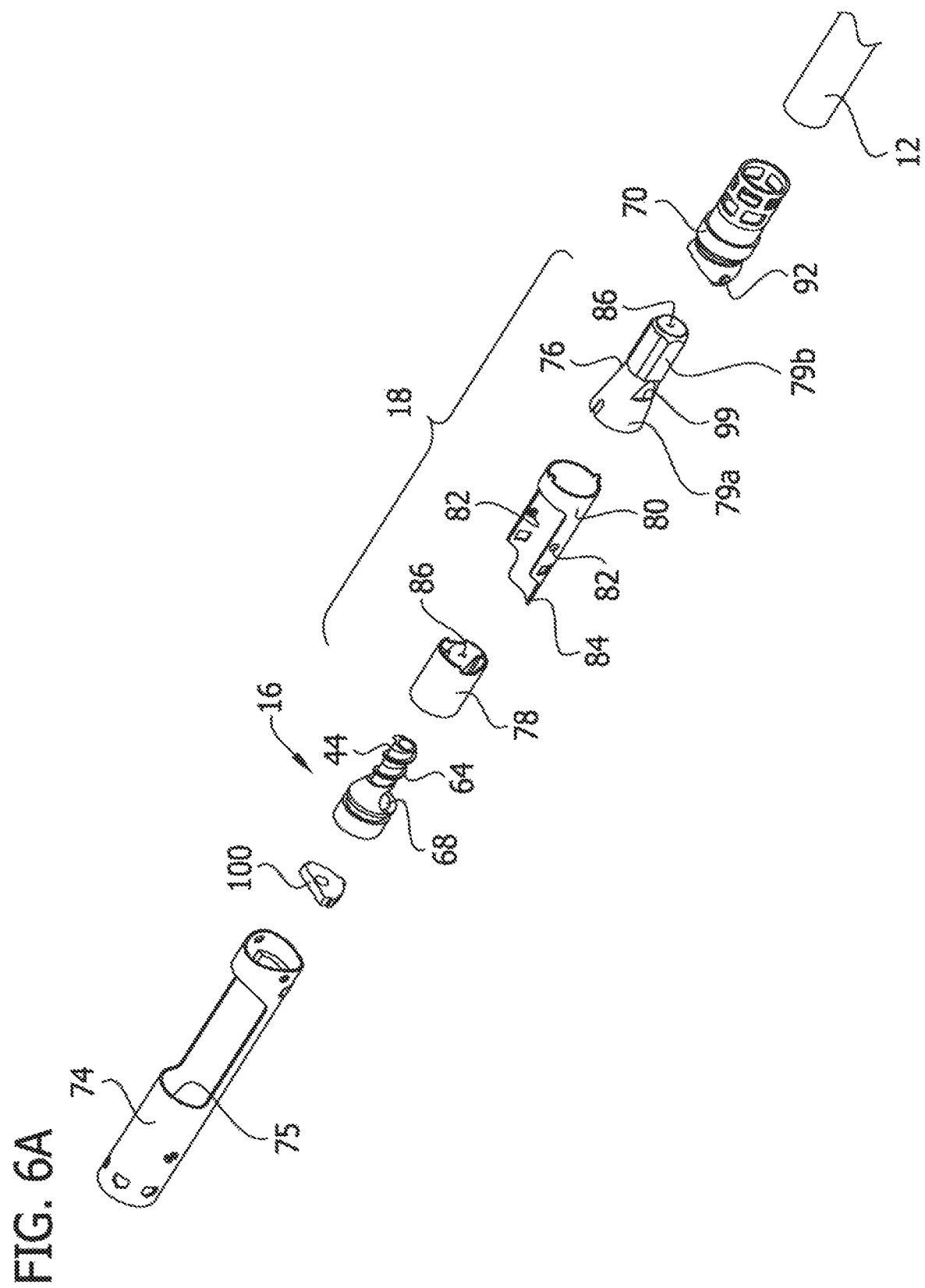
FIG. 6 is an exploded perspective of the distal end portion of the tissue-removing catheter.
FIG. 6B is an enlarged, exploded perspective of the cutter housing of the tissue-removing catheter.

The cutter housing 74 is hingedly attached to the deployment adaptor 70 at its proximal end via a hinge connector 92 (e.g., a hinge pin, a trunnion, a living hinge, or the like) on the deployment adaptor 70 (see FIG. 6A). The hinge connector 92 enables the cutter housing 74 to pivot (broadly, deflect) relative to the catheter body 12, the cutter adaptor 18, and the cutter generally transverse to the longitudinal axis $LA_1$ of the catheter body 12 for deploying and retracting the cutter 16, as shown in FIGS. 2-5. A tip (not shown) of the catheter 10 may be secured to the distal end of the cutter housing 74, such that the tip moves with the cutter housing.

To open the deployment mechanism 24, thereby deploying the cutter 16, the driveshaft 20 is moved proximally, such as by moving the lever 40 on the handle 32. As the driveshaft 20 is moved proximally, the opening ramp follower 90 in the cutter housing 74 runs a long the exterior of the cutter adaptor 18 (more specifically, the exterior of the proximal tube piece 76) causing the cutter housing 74 to pivot (broadly, deflect) relative to the catheter body 12 and about the hinge axis. As the cutter housing 74 deflects, the cutting tip 50 of the cutter 16 extends through the cutter window 75 in cutter housing, whereby the cutting tip 50 is exposed outside the cutter housing. As shown in FIG. 4A, when the cutter 16 is in the deployed configuration, the longitudinal axis $LA_2$ of the cutter extends at an angle $\alpha_2$ offset from a central longitudinal axis LA of the cutter housing 74. This offset angle $\alpha_2$ may measure from about 5 degrees to about 15 degrees. As seen in FIGS. 4 and 5, in the deployed position, only a circumferential portion of the cutting tip 50 (i.e., an exposed circumferential portion) extends through the window 75, while the remaining circumferential portion of the cutting tip does not extend through the window and is not exposed (i.e., a non-exposed circumferential portion). The ratio of the exposed circumferential portion to the non-exposed circumferential portion is the effective-exposure of the cutting tip 50. In the illustrated embodiment, less than half of the circumference of the cutting tip 50 is exposed, at any instantaneous time, as the cutter 16 is rotating, and therefore, the effective-exposure of the cutting tip is less than 50%.

Referring to FIGS. 2 and 4B, the illustrated embodiment includes stops 99 (only one stop is visible in FIGS. 2 and 4B on the cutter adaptor 18, and more specifically, on an exterior of the proximal tube piece 76 to restrict proximal movement of the cutter adaptor relative to the cutter housing 74. In the illustrated embodiment, the stops 99 are defined by notches formed in the exterior of the proximal tube piece. The distal end of the catheter body 12, more specifically, the distal end of the deployment adaptor 70 in the illustrated embodiment, engages the stops 99 when the cutter 16 is fully deployed to inhibit further proximal movement of the cutter adaptor 18. Alternatively, the distal and of the deployment adaptor 70 engages the stops 99 if there is an attempt to force the cutter adaptor 18 proximally beyond its fully deployed position.

To close the deployment mechanism, thereby retracting the cutter 16 in the stowed configuration (as shown in FIGS. 1-3), the driveshaft 20 is moved distally from its proximal position, such as by moving the lever 40 on the handle 32, which may also turn off the cutter driver 30 and stop rotation of the cutter 16. As the driveshaft 20 is moved distally, which moves the cutter 16 and hence the cutter adaptor 18 distally, the closing ramp follower 88 in the cutter housing 74 runs along the tongue 84 at the distal end of the cutter adaptor, thereby driving the cutter housing to pivot about the hinged axis toward the closed position. As the cutter housing 74 pivots toward the cutter 16, the cutting tip 50 reenters the cutter housing through the cutter window 75. When the cutter 16 is in its fully retracted position inside the cutter housing 74, the distal end of the tongue 84 is received in a tongue slot 98 to inhibit pivoting of the cutter housing 74 about the hinge axis. When the driveshaft 20 is moved proximally, the tongue 84 withdraws from the tongue slot 95 to allow the cutter housing 74 to pivot about the hinge axis. The shape of the tongue 84 and closing ramp follower 88 allows the cutter housing 74 to first pivot (upon retraction of the cutter 16) and then allows the cutter to move axially into the cutter housing from the cutter window 75. The opposite happens when the cutter 16 is deployed. The cutter 16 first moves axially into the cutter window 75 and then the cutter housing 4 is then pivoted to expose the cutting tip 50. It will be understood that the force for both deploying and retracting the cutter 16 is provided entirely by the user through movement of the cutter 16, cutter adaptor 18 and drive shaft 20.

As set forth above, and explained in more detail below in one embodiment it is desirous to have the removed tissue move proximally through the cutter 16 (e.g., move into the axial cavity 52 and through the eccentric opening 68 in the cutter) and into the cutter adaptor 13 where it can be picked up and transported proximally within the catheter 10 by the stem thread 64 and the driveshaft thread 22. To further facilitate proximal movement of the removed tissue, the illustrated catheter 10 also includes a guard 100 (broadly, a tissue deflector) connected to the cradle-shaped bearing member 80 to block removed tissue that has entered the axial cavity 52 from reversing direction (i.e., moving distally) and exiting the axial cavity back through the distal end of the cutter 16. The guard 100 is disposed generally immediately distal of the cutting tip 50 of the cutter 16, and extends radially inward from the bearing member 80 toward the cutter window 75 in the cutter housing 74 to cover the non exposed circumferential portion of the annular cutting tip 50 that is disposed below the cutter window 75 when the cutter is deployed. In other embodiments, the guard 100 may cover more or less than the non-exposed circumferential portion.

Figure 17:
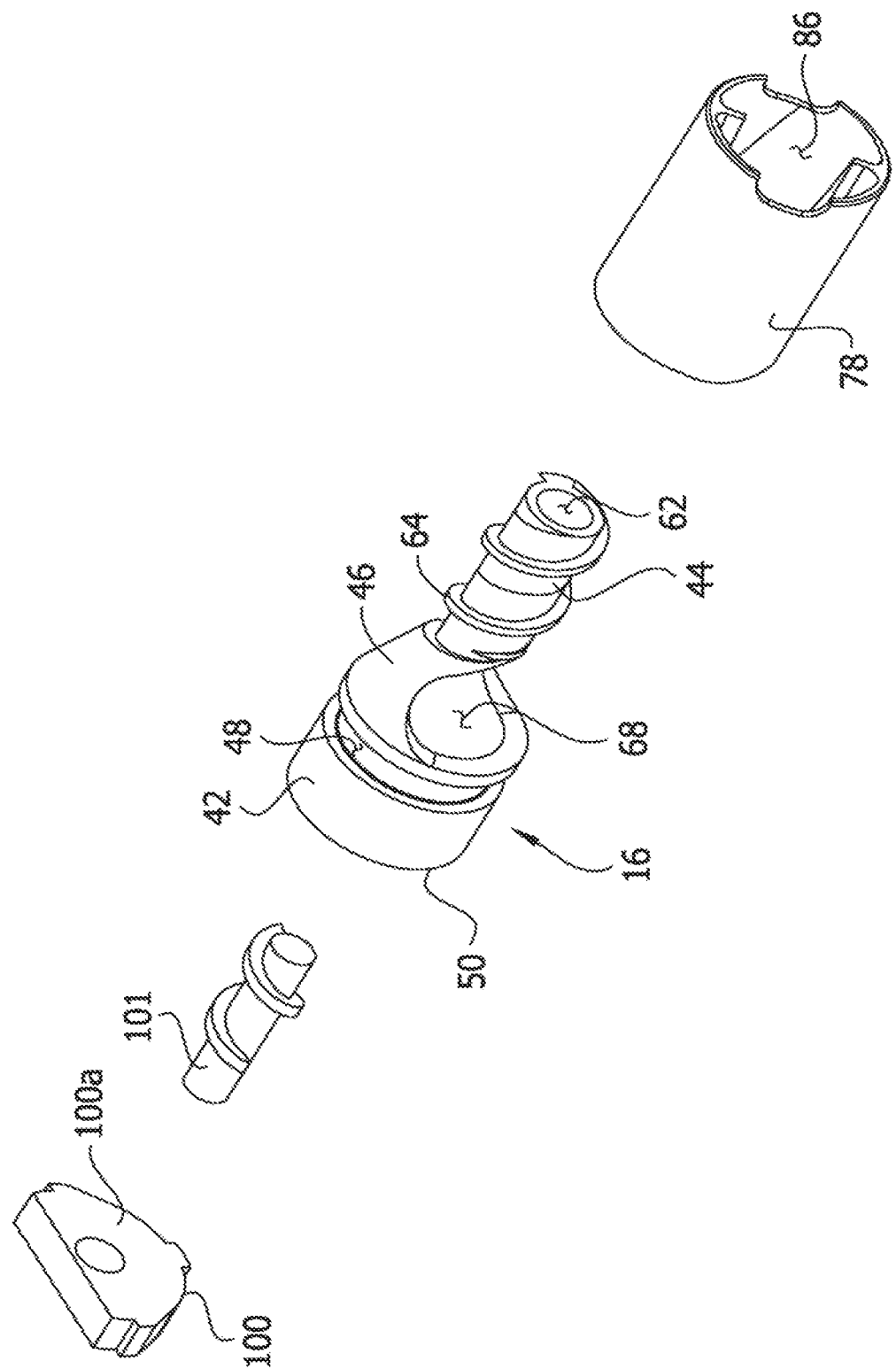
FIG. 17 is an enlarged, exploded perspective of the cutter and a distal tube piece of the tissue-removing catheter of FIG. 1, including a second embodiment of a guard of the tissue-removing catheter.
Figure 18:
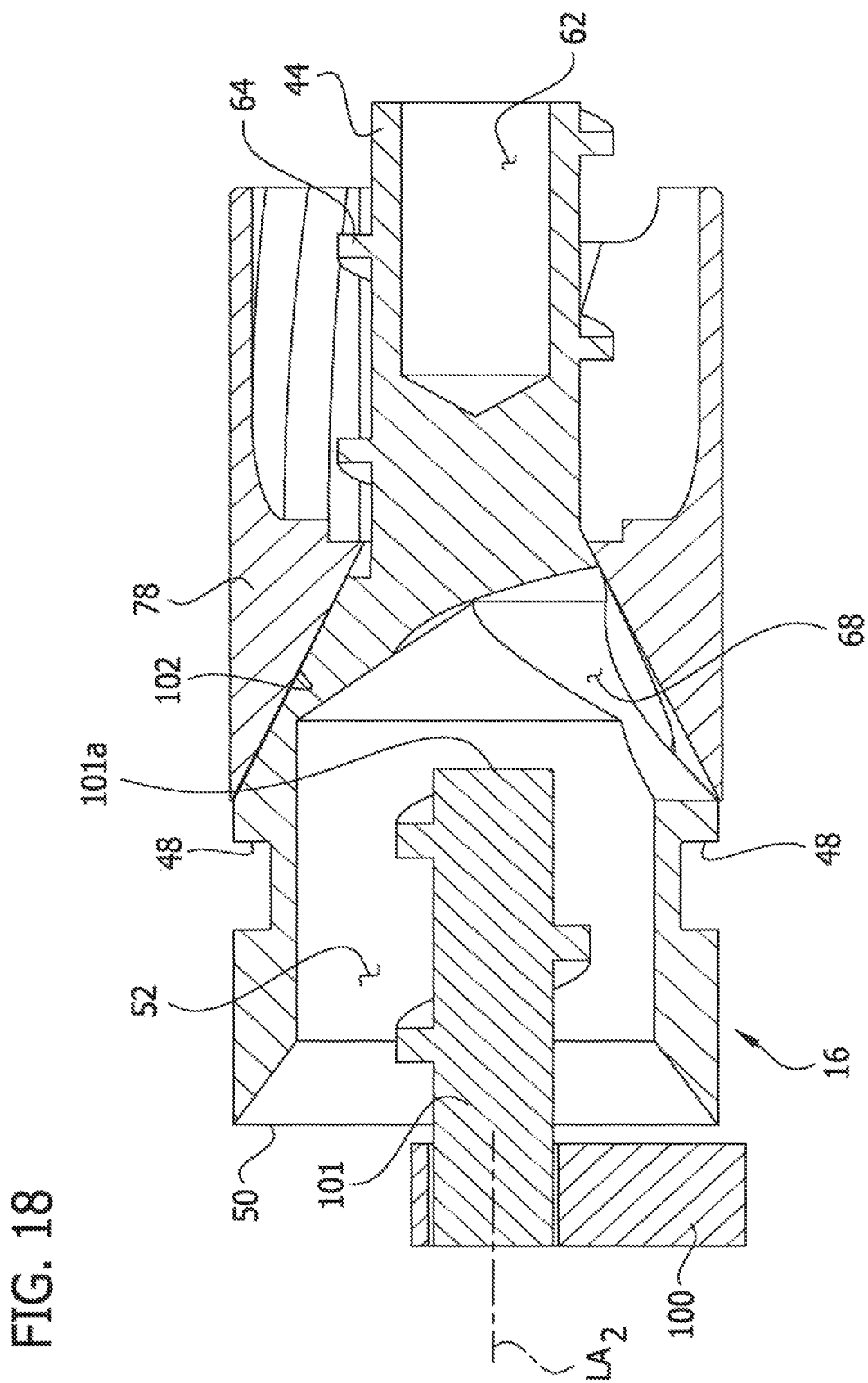
FIG. 18 is a longitudinal section taken through the assembled cutter, distal tube piece, and guard of FIG. 17.

Referring to FIGS. 17 and 18, the guard 100 may include an externally threaded auger member 101 extending outward from a face 100a of the guard that opposes the cutting tip 50. As shown in FIG. 18, the auger member 101 extends through the annular cutting tip 50 and into the axial cavity 52. The auger member 101 is coincident with the central longitudinal axis $LA_2$ of the cutter 16. A terminal end 101a of the auger member 101 is disposed within the axial cavity 52. The auger member 101 is stationary and the cutter 16 rotates around the auger member 101 so that removed tissue that accumulates in the axial cavity and wraps around the auger member will be directed proximally, toward the eccentric opening 68 in the cutter, it is understood that the guard 100 and/or the auger member 101 may be omitted from the catheter 10.

As explained in more detail below, in the embodiments illustrated in FIGS. 1-12, the cutter adaptor 18 (or at least a portion(s) thereof) constitutes functions as a "shearing member," in addition to constituting (i.e., functioning as) a "camming element" of the deployment mechanism 24, it is understood that in at least some embodiments, the cutter adaptor 18 may constitute a "shearing member," as described below, and not constitute a "camming element" or otherwise form part of the deployment mechanism. Moreover, some other component may be a camming element, or the camming element may be omitted. Likewise, it is understood that in at least some embodiments, the cutter adaptor 18 may constitute a "camming element" or otherwise form part of the deployment mechanism, and not constitute a "shearing member." Moreover some other component may be a shearing member, or the shearing member may be omitted.

Figure 19:
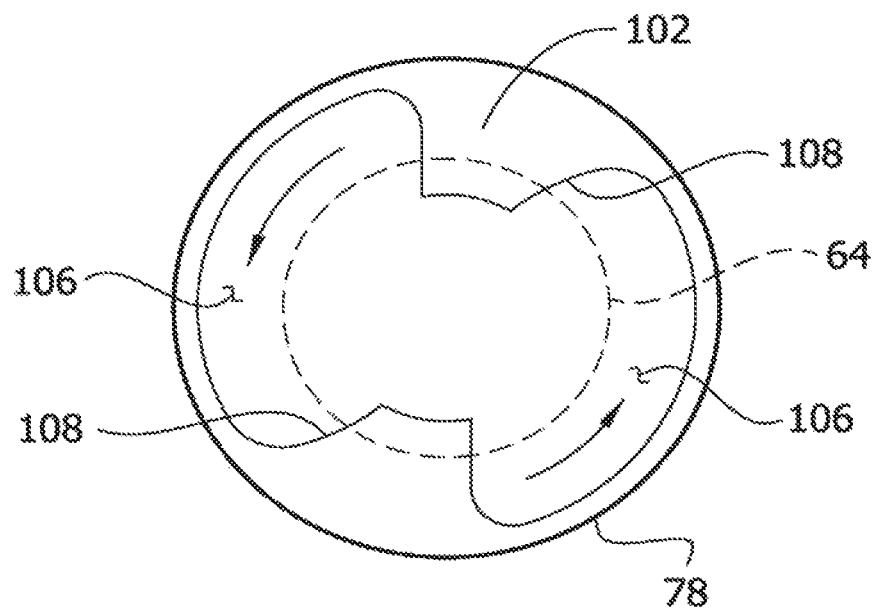
FIG. 19 is an enlarged front elevation of the distal tube piece of the tissue-removing catheter of FIG. 1, with an external thread of a cutter stem shown in broken lines.
Figure 20:
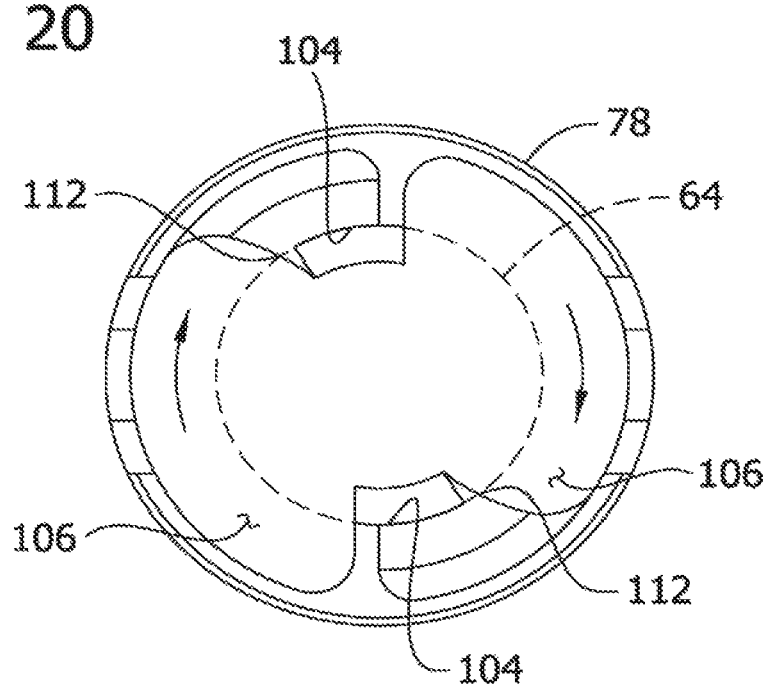
FIG. 20 is an enlarged rear elevation of the distal tube piece of the tissue-removing catheter of FIG. 1, with an external thread of a cutter stem shown in broken lines.

The distal tube piece 78 of the present illustrated cutter adaptor 18 constitutes the "shearing member." Referring to FIGS. 19-21, in this embodiment the distal tube piece 78 has an internal bearing surface 102 at a distal end portion thereof that engages the exterior surface of the transitional portion 46 of the cutter 16, and a counter bore 104 extending through a proximal end toward the internal bearing surface and forming part of the internal passage 86 of the cutter adapter 18. (The internal bearing surface 102 is also visible in FIGS. 3 and 5, among other views, but is not labeled.) As seen from FIG. 21, the internal bearing surface 102 has a generally conical shape, corresponding generally to the conical shape of the exterior surface of the transitional portion 46 of the cutter 16. Circumferentially spaced apart channels 106 extend longitudinally through the bearing surface 102 to form shearing edges 108. In the present embodiment, seen best in FIGS. 19-21, the distal tube piece 78 (functioning as the "shearing member") includes two longitudinally-extending channels 106 forming two diametrically-opposing shearing edges 108, although it is understood that the distal tube piece 78 may have one shearing edge or more than two shearing edges without departing from the scope of the present invention. As can be seen from FIGS. 3, 5, and shown best in FIG. 21, a cutter shearing edge 110 partially defining the eccentric opening 68 in the cutter 16 interacts with the shearing edges 108 as the cutter rotates. That is, as tissue removed from the body lumen (e.g., blood vessel) passes through the eccentric opening 68 in the cutter 16, the removed tissue is sheared or cleaved between the respective shearing edges 108, 110. This shearing facilitates movement of the removed tissue proximally into the cutter adaptor 18 and toward the stem thread 64 and/or the driveshaft thread 22. In the illustrated embodiment, the removed tissue is sheared between the shearing edges 108, 110 at about every 0.5 revolutions of the cutter 16.

Figure 10:
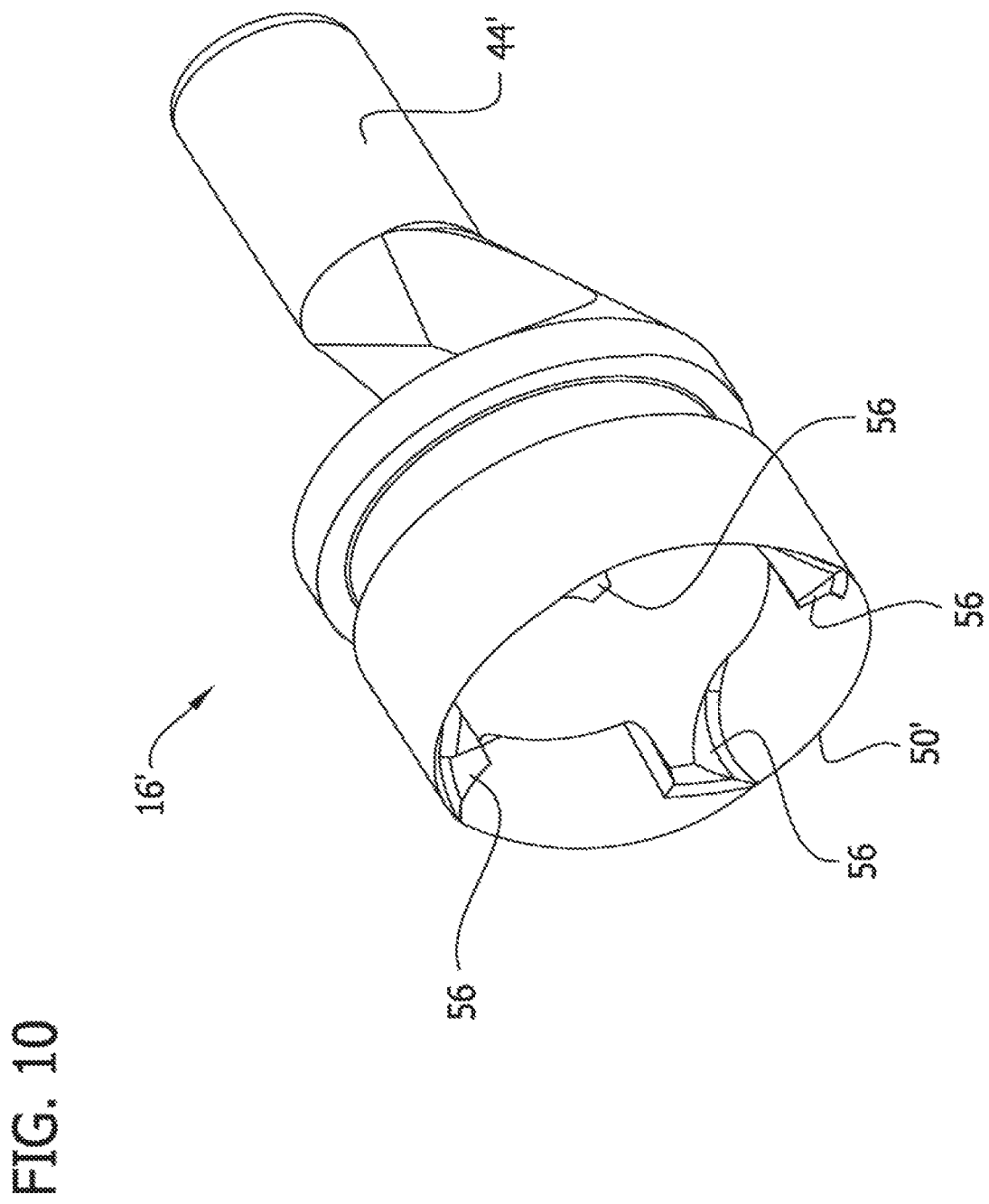
FIG. 10 is a front perspective of a second embodiment of a cutter for the tissue-removing catheter of FIG. 1.
Figure 11:
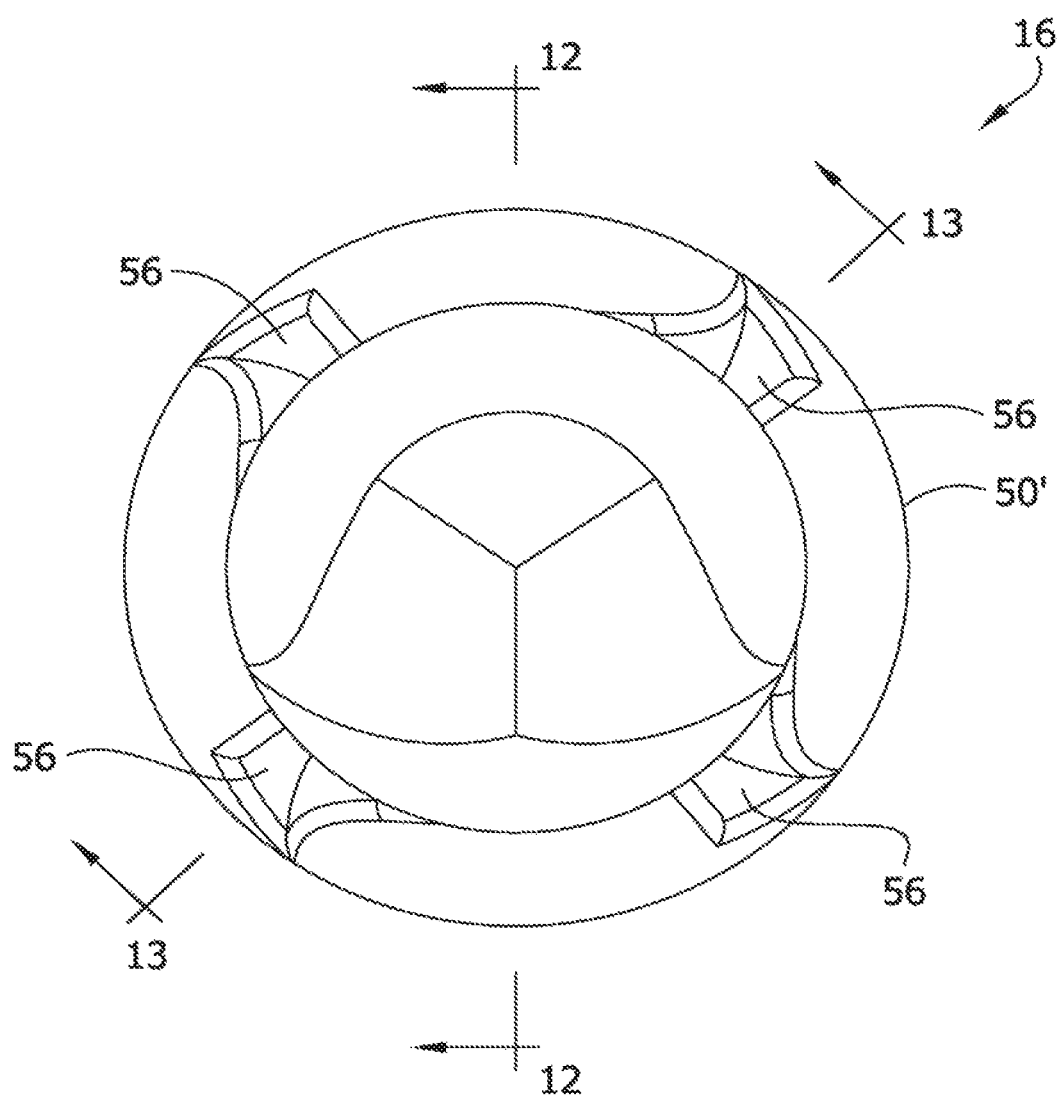
FIG. 11 is a front elevation of the cutter of FIG. 10.
Figure 12:
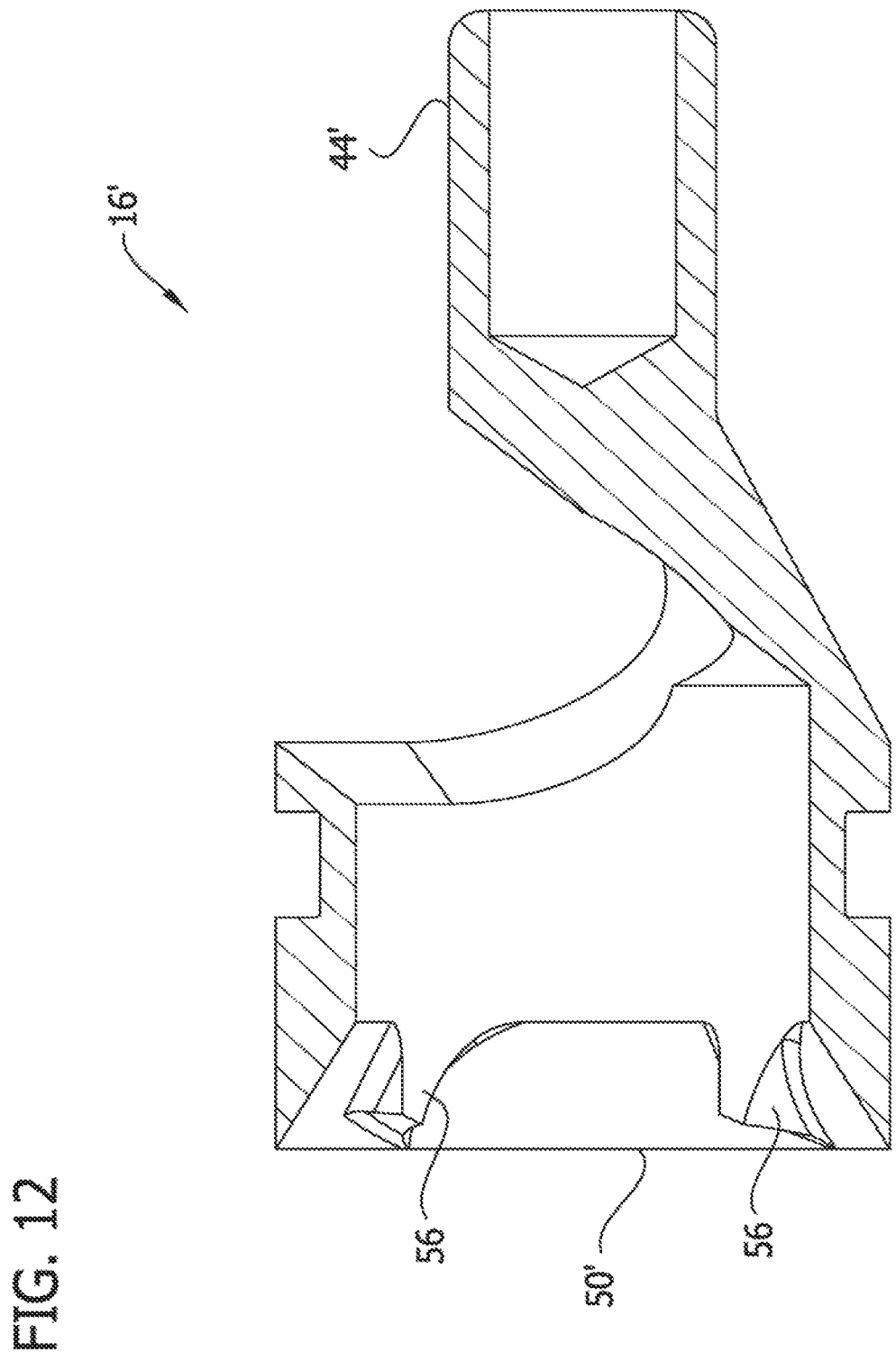
FIG. 12 is a longitudinal section of the cutter taken in the plane indicated by line 12-12 in FIG. 11.
Figure 13:
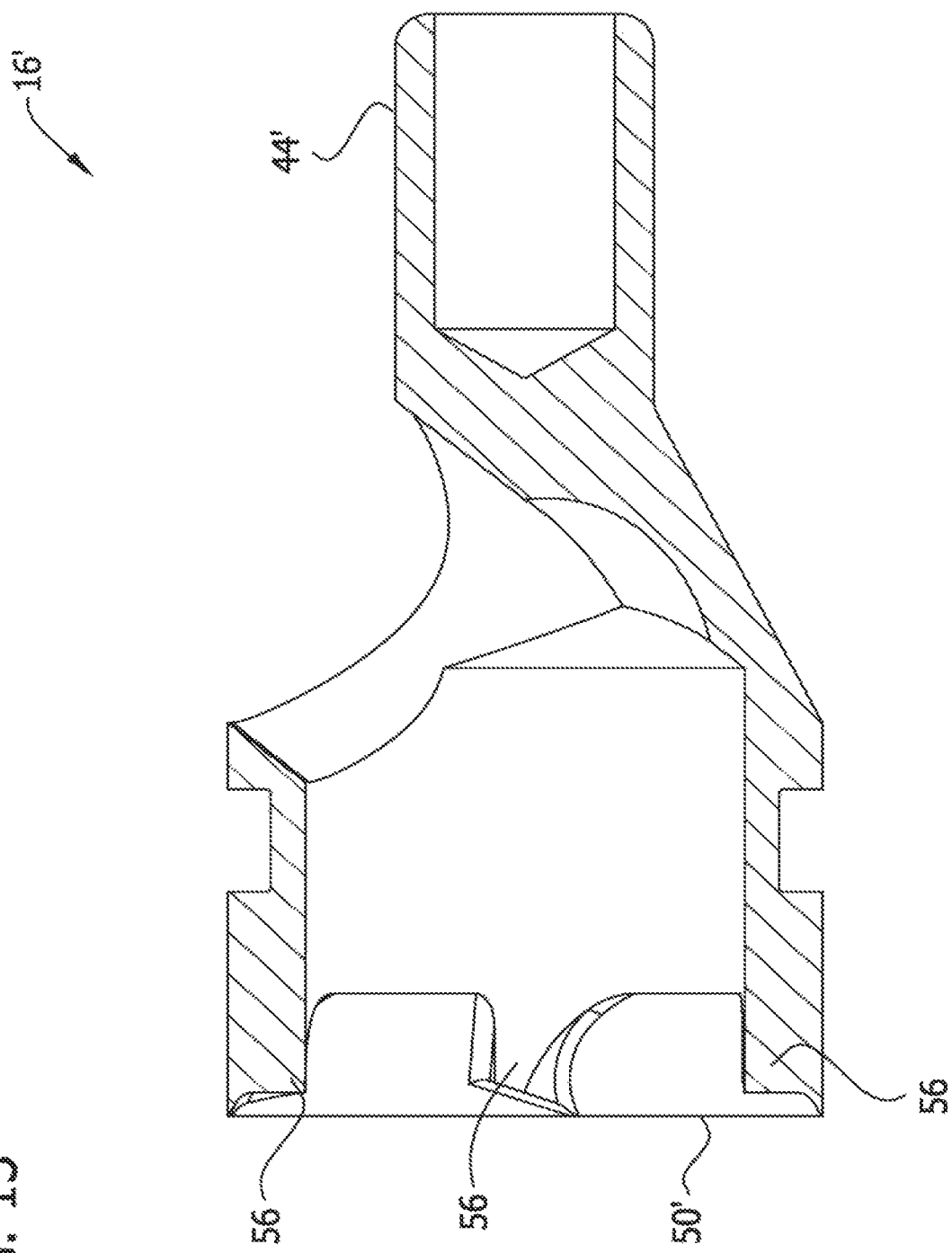
FIG. 13 is longitudinal section of the cutter taken in the plane indicated by line 13-13 in FIG. 11.

Referring to FIGS. 19-21, the counterbore 104 is sized and shaped for receiving the cutter stem 44 of the cutter 16. The longitudinal channels 106 also extend through the interior surface defining the counterbore 104 to form longitudinal shearing edges 112 at the counterbore 104. As set forth above, in this embodiment the cutter stem 44 includes the helical, exterior thread 64, which in the present embodiment is a right-handed thread. The exterior thread 64 (as shown in broken lines in FIGS. 19 and 20) on the cutter stem 44 interacts with the shearing edges 112 at the counterbore 104 as the cutter 16 rotates (i.e., clockwise rotation as shown in FIGS. 10 and 11) to shear and pinch removed material therebetween to facilitate proximal movement of the removed tissue within the cutter adaptor 18. In the present embodiment (shown best in FIGS. 19-21), the major diameter of the stem thread 64 is slightly less than the inner diameter of the counterbore 104, so that there is smell radial gap (i.e., small amount of play) between the stem thread and the shearing edges 112. The radial gap is such so as not to inhibit or impede rotation of the stem 44 in the counterbore 104, and at the same time provide this shearing or pinching of removed material between the stem thread 64 and the shearing edges 112 to facilitate proximal movement of the removed tissue.

In the present embodiment as seen best in FIG. 21), the internal passage 86 defined by the proximal tube piece 76 has a diameter (i.e., inner cross-sectional dimension of the proximal tube piece) at the transitional portion 79a of the proximal tube piece 76 that tapers proximally to a constant, uniform diameter at the proximal portion 79b of the proximal tube piece. The tapering internal passage 86 at the transitional portion 79a is significantly greater than the major diameter of the stem thread 154 and/or the driveshaft thread 22 such that tissue may pass between the interior surface of the transitional portion of the proximal tube piece and the stem thread and/or the driveshaft thread without undergoing significant shear. The diameter of the internal passage 86 at the proximal portion 79b of the proximal tube piece 76, on the other hand, is slightly greater than the major diameter of the driveshaft thread 22 so as not to inhibit or impede rotation of the driveshaft 20 in the proximal tube piece 76, and at the same time, substantially inhibit removed tissue from passing between the driveshaft thread 64 and the interior surface defining the constant inner diameter of proximal tube piece. In this way, the driveshaft 20 effectively functions as an auger or screw conveyor in the proximal portion 79b of the proximal tube piece 76. In another embodiment, the major diameter of the portion of the driveshaft thread in the transitional portion 79a may taper to correspond to the taper of the internal passage 86 so that the driveshaft 20 also effectively functions as an auger or screw conveyor in the transitional portion 79a. In yet another embodiment, such as the embodiment illustrated in FIGS. 23-27 and discussed below, the proximal tube piece may have a substantially uniform inner diameter (i.e., substantially non tapering) that is slightly greater than the major diameter of the stem thread 64 and/or the driveshaft thread 22, and channels may extend longitudinally through the interior surface thereof to define shearing edges, similar to the shearing edges 112 of the counterbore 104.

Figure 25:
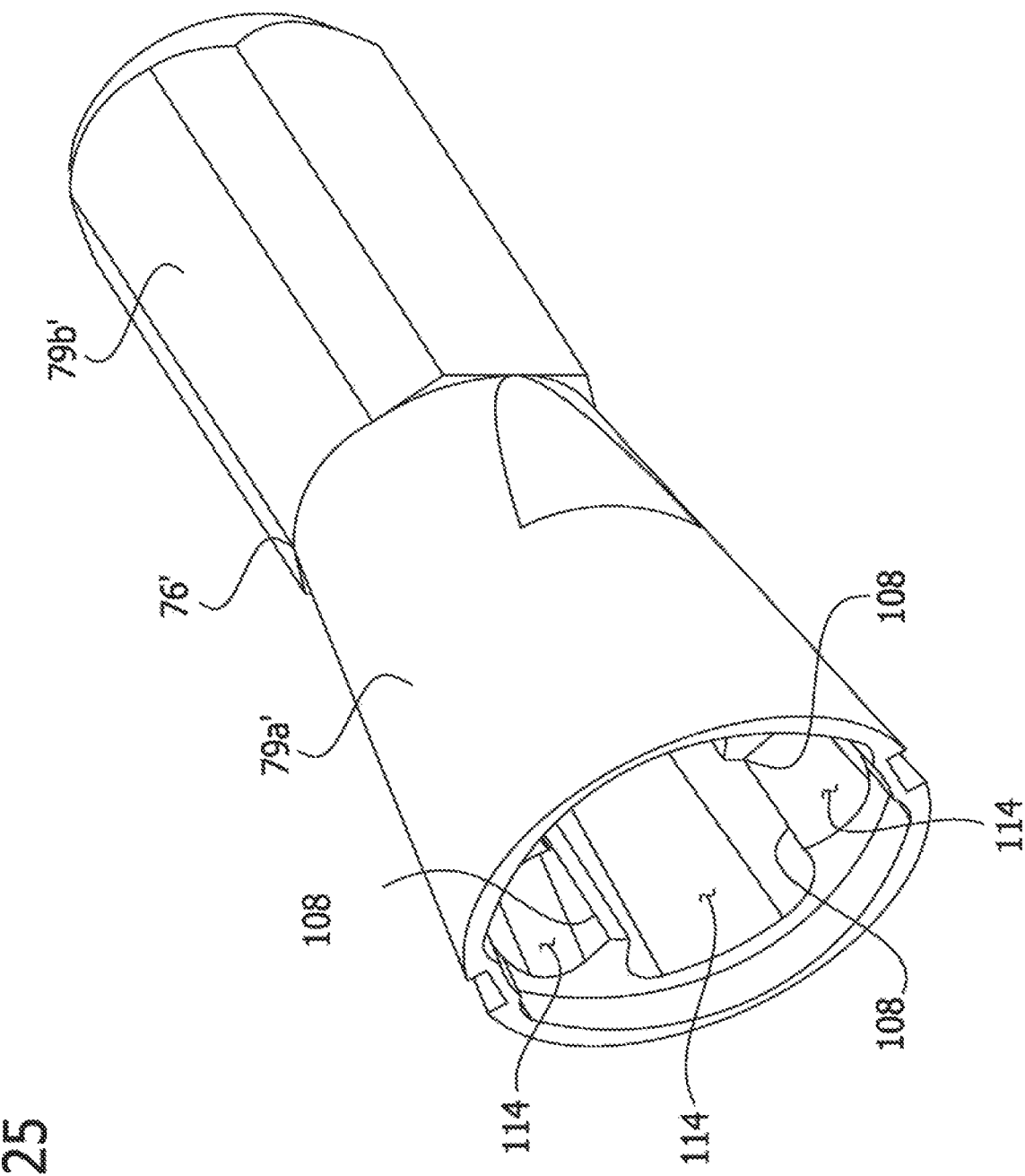
FIG. 25 is an enlarged front perspective, of as second embodiment of a proximal tube piece for the tissue-removing catheter of FIG. 1.
Figure 26:
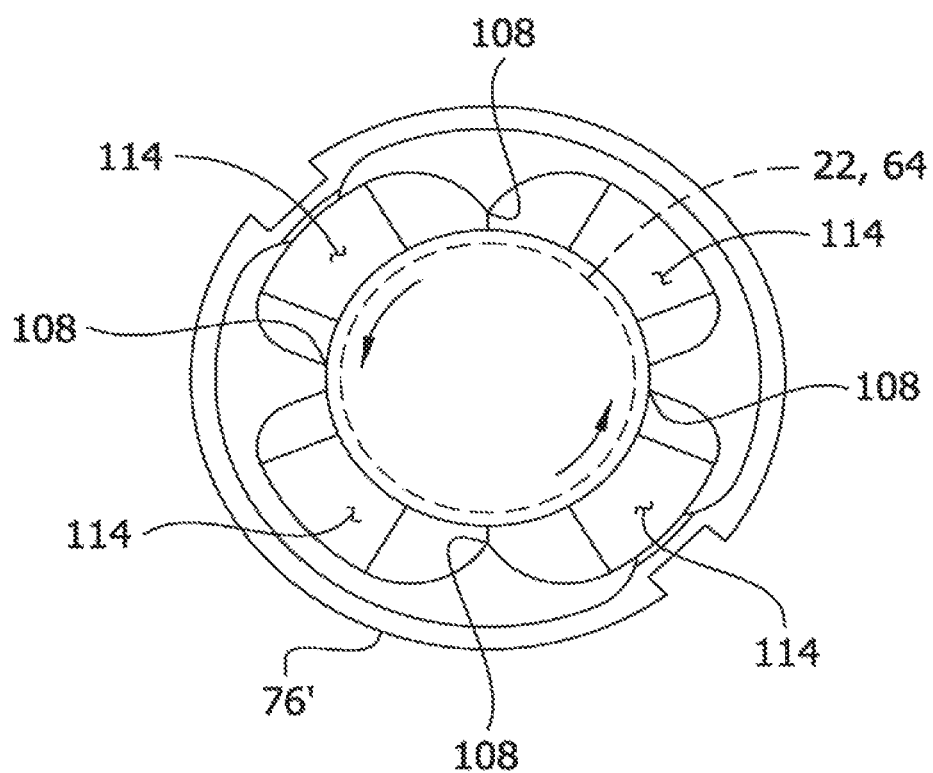
FIG. 26 is a front elevation of the proximal tube piece of FIG. 25, with an external thread of a driveshaft shown in broken lines.

Referring to FIGS. 22-27, second embodiments of the proximal and distal tube pieces are indicated by reference numerals 76' and 78'. The second embodiment of the distal tube piece 78' is shown in FIGS. 22-24 and 27, and the second embodiment of the proximal tube piece 76' is shown in FIGS. 25 and 26. These embodiments of the proximal and distal tube pieces 76', 78', respectively, may be used with the catheter illustrated in FIGS. 1-21 by substituting the proximal and distal tube pieces 76, 78, respectively, of the previous embodiment with the respective tube pieces 76', 78' of the present embodiment. The present proximal and distal tube pieces 76', 78', respectively, are similar to the previously disclosed proximal and distal tube pieces 75, 78, and like components are indicated by corresponding reference numerals including prime symbols. In general, the operation of the catheter including one or both second embodiments of the proximal and distal tube pieces 76' and 78' for removing tissue from a body lumen may be substantially similar to the exemplary operation set forth above with respect to the first embodiment.

Referring to FIGS. 22-24 and 27, one difference between the present distal tube piece 78' and the previously described distal tube piece 78 is that the distal tube 78' piece includes four (4) circumferentially spaced apart channels 106' extending longitudinally through the bearing surface 102' and the interior surface of the distal tube piece to define four (4) shearing edges 108' at the bearing surface 102', as opposed to two (2) shearing edges 108 in the other embodiment, and four (4) shearing edges 112' extending proximally within the distal tube piece 78'. As shown in FIGS. 14 and 15, two of the four shearing edges 112' are defined by the intersection of the counterbore 104' and two of the channels 114', and the remaining two of the four shearing edges are defined by the intersection of two adjacent channels 106'. The shearing edges 108', 112' may be formed in other ways without departing from the scope of the present invention. As with the shearing edges 108 in the first embodiment, the shearing edges 108' interact with the cutter shearing edge 110 to shear removed tissue passing through the eccentric opening 68 in the cutter 16. As opposed to the first embodiment, however, removed tissue is sheared at a quarter-revolution of the cotter 16. Moreover, as with the shearing edges 112 in the first embodiment, the shearing edges 112' interact with the stem thread 64 to shear or pinch removed tissue in the cutter adaptor to facilitate movement of the tissue proximally, toward the threaded driveshaft 20.

Figure 27:
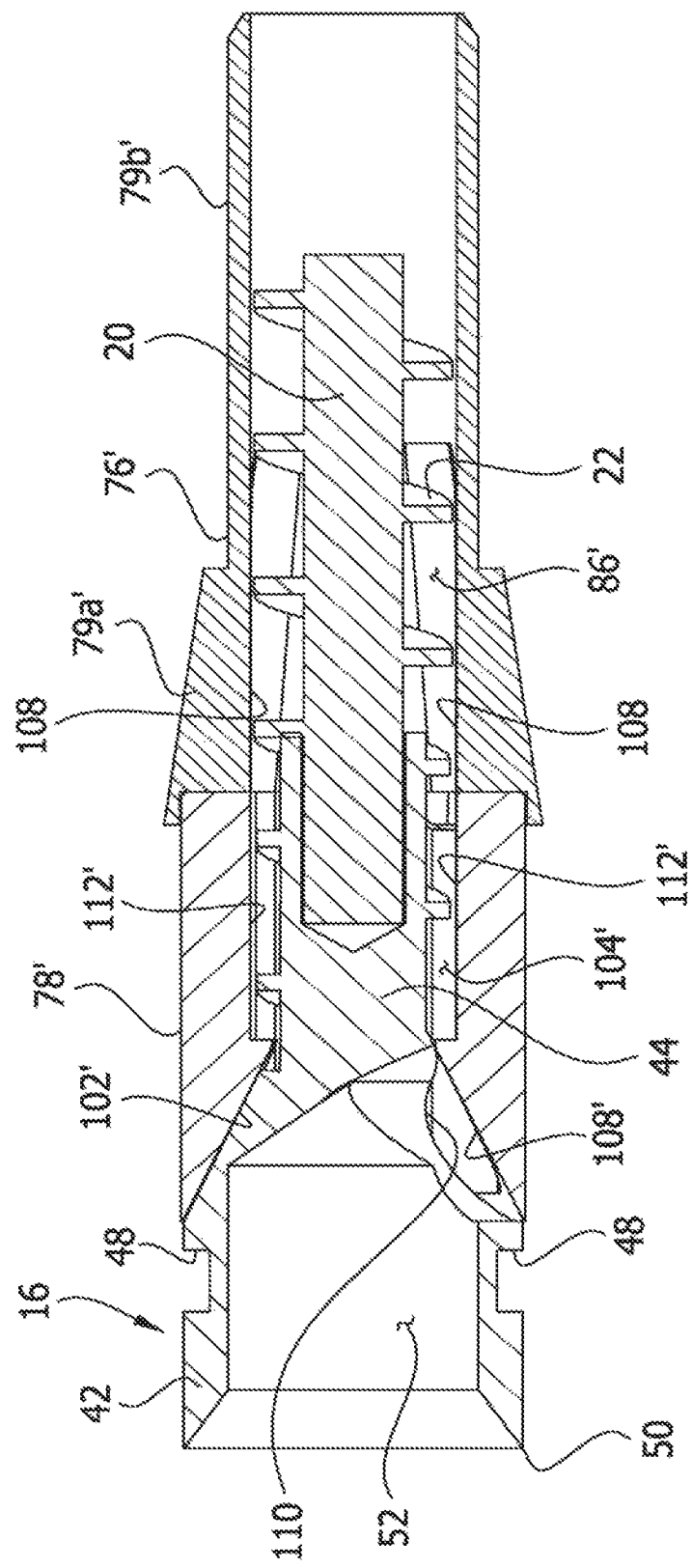
FIG. 27 is an enlarged longitudinal section similar to FIG. 21, including the second embodiments of the proximal and distal tube pieces.
Figure 28:
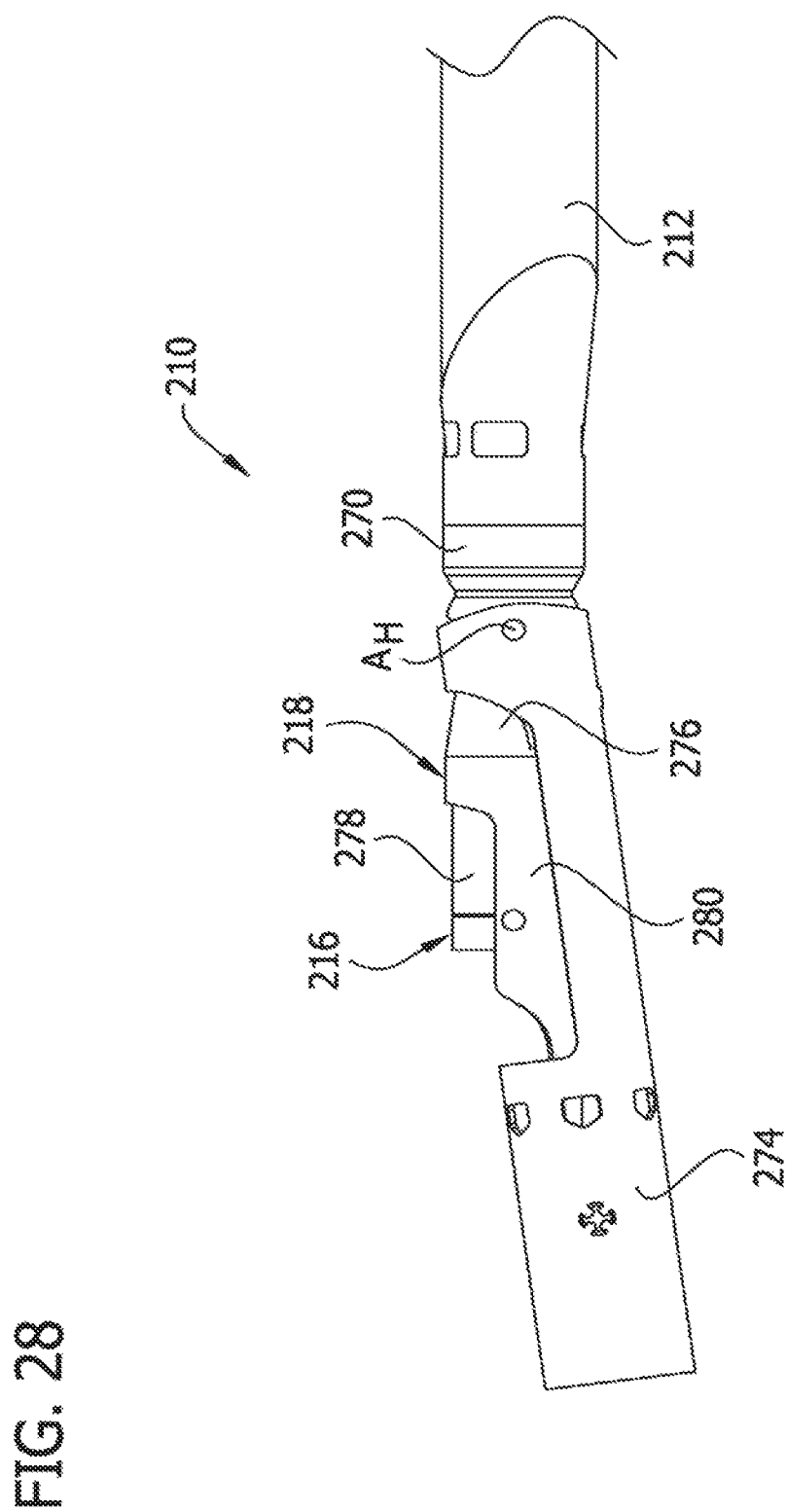
FIG. 28 is an enlarged side elevation of a distal end portion of a second embodiment of the tissue-removing catheter, with a cutter of the tissue-removing catheter in a deployed position.

Referring to FIGS. 25-27, one difference between the present the proximal tube piece 76' and the first proximal tube piece 76 is that the present proximal tube piece has a substantially uniform inner diameter (i.e., substantially non-tapering) along its length that is slightly greater than the major diameter of the stem thread 64 and/or the driveshaft thread 22. As shown in FIGS. 25 and 26, circumferentially spaced apart channels 114 (not present in the first embodiment) extend longitudinally through the interior surface of the proximal tube piece 76' to define shearing edges 115, similar to the shearing edges 112' of the counterbore 104'. More specifically, in the illustrated embodiment these channels 114 extending longitudinally through the transitional portion 79a' of the proximal tube piece 76' that has a tapered exterior surface, but the channels do not extend through the proximal portion 79b' of the proximal tube piece that is received in the distal end (e.g., the deployment adaptor 70) of the catheter body 12. The shearing edges 108' in the proximal tube piece 76' may be extensions of the shearing edges 112' of the counterbore 104'. The exterior thread 22 on the driveshaft interacts with the shearing edges 108 as the cutter 16 and driveshaft rotates to shear or pinch tissue therebetween to facilitate proximal movement of the removed tissue.

In an exemplary operation, the catheter 10 is inserted into the body lumen (e.g., artery) such that the cutter 16 is positioned adjacent the target site. Fluoroscopy or other imaging techniques may be used to facilitate placement of the catheter 10 in the body lumen. During placement of the catheter 10 in the body lumen, the deployment mechanism 24 is closed and the cutter 16 is in the stowed position. At the target site, the deployment mechanism 24 is opened, such as by moving the lever 40 on the handle 33 proximally, to impart proximal movement of the driveshaft 20 relative to the catheter body 12 and the cutter housing 74, whereby the cutter adaptor 18 and the cutter 16 are also moved proximally relative to the cutter housing. As the cutter adaptor 18 moves proximally, the tongue 84 at the distal end of the cutter adaptor withdraws from the tongue slot 98 in the cutter housing 74, and opening ramp follower 90 in the cutter housing runs along the exterior surface of the proximal tube piece 76. Thus, the cutter adaptor 18, more specifically proximal tube piece 76, acts as a camming element for opening the deployment mechanism 24. As the proximal tube piece 76 rides along the opening ramp follower 90, the cutter housing 74 pivots relative to the cutter adaptor 18, the cutter 16, and the catheter body 12, about the hinge axis and a portion of the cutting tip 50 of the cutter extends through the cutter window 75 defined by the cutter housing. As explained above, an urging mechanism (not shown) may urge the cutting tip 50 toward the wall of the body lumen, and the offset cutter housing 74 may also facilitates urging of the cutter toward the wall of the body lumen.

In one example, deploying the cutter 16 using the lever 40 also actuates or turns on the cutter motor 30 to impart rotation of the driveshaft 20 and the cutter. With the cutter 16 deployed and rotating, the catheter 10 is moved distally within the body lumen, and the rotating cutting tip 50 removes the tissue (e.g., plaque) from the body lumen (e.g., from en artery). As the tissue is being removed, the removed tissue moves through the annular cutting tip 50, into the axial cavity 52 in the cutter 16, and then passes into the eccentric opening 68. Using the catheter 10 illustrated in FIGS. 1-21, at about every half revolution of the cutter 16, the cutter shearing edge 110 passes by one of the shearing edges 108 of the internal bearing surface 102 to shear the removed material disposed at that shearing location. The sheared tissue moves proximally within the cutter adaptor 18, more specifically, within the counterbore 104, where the rotating stem thread 64 interacts with the shearing edges 112 in the counterbore to pinch or shear the removed tissue and facilitate proximal movement of the tissue within the cutter adaptor, toward the driveshaft thread 22 and the tissue-transport passage 14 of the catheter body. Within the tissue-transport passage 14, the removed tissue continues to be moved proximally by the driveshaft thread 22, which functions as an auger-like or conveyor-like transport mechanism.

Using the catheter 10 illustrated in FIGS. 1-21, and substituting the respective proximal and distal tube pieces 76, 78, respectively, for the proximal and distal tube pieces 76', 78', the cutter shearing edge 110 passes by one of the shearing edges 108' of the internal bearing surface 102' to shear the removed material disposed at that shearing location. The sheared tissue moves proximally within the counterbore 104' of the distal tube piece 78', where the rotating stem thread 64 interacts with the shearing edges 112' in the counterbore to pinch or shear the removed tissue and facilitate proximal movement of the tissue toward proximal tube piece 76. Within the proximal tube piece 76, the rotating driveshaft thread 22 interacts with the shearing edges 106 to pinch or shear the removed tissue and facilitate proximal movement of the tissue-transport passage 14. Within the tissue-transport passage 14, the removed tissue continues to be moved proximally by the driveshaft thread 22, which functions as an auger-like or conveyor-like transport mechanism.

After completing a pass through the target site and removing a strip of tissue from the body lumen, the deployment mechanism 24 may be closed and the cutter motor 30 turned off (or alternatively, the motor may remain on) by moving the driveshaft 20 distally relative to the catheter body 12 using the lever 40 on the handle 32. As the driveshaft 20 is moved distally, the closing ramp follower 88 runs along the tongue 84 to drive pivoting of the cutter housing 74 relative to the cutter adaptor 18 and the cutter 16 about the hinge axis $A_H$. When the cutter 16 is in its fully stowed position inside the cutter housing 74 (as shown, for example, in FIGS. 1-3), the distal end of the tongue 84 is received in the tongue slot 98 in the cutter housing 74 and the cutting tip 50 is received in the cutter housing, and unexposed. With the cutter motor 30 turned off (in one embodiment) and the cutter 16 in the retracted position, the catheter 10 is moved proximally within the body lumen to allow for another pass through the target site.

Referring to FIGS. 28-33, another embodiment of a tissue-removing catheter for removing tissue from a body lumen is generally indicated at 210. This embodiment includes features that are similar, if not identical, to features disclosed above with respect to the catheter 10 disclosed above. Components of the present embodiment that are similar or identical to components of the catheter 10 are indicated by corresponding reference numerals plus 200.

The present catheter 210 includes an elongate catheter body 212 that may be identical to the catheter body 12, disclosed above. Other components of the present catheter 210 that may be identical to like components of the catheter 10 in both structure and function and therefore will not be explained in any more detail, include: the threaded driveshaft 220, the cutter housing 274 (including the closing and opening ramp followers 288, 290) hinged to the deployment adaptor 270 and pivotable about hinge axis $A_H$, the cradle-shaped bearing member 280, and the proximal tube piece 276. As explained below, the following components of the present catheter 210 are similar to like components of the catheter 10, albeit these components differ from the previously described components in one or both of structure and function: the cutter 216 and the distal tube piece 278 (and thus, the cutter adaptor 218, although the proximal tube piece 276 and the bearing member 280 are identical to the respective proximal tube piece 76 and the bearing member 80).

Figure 31:
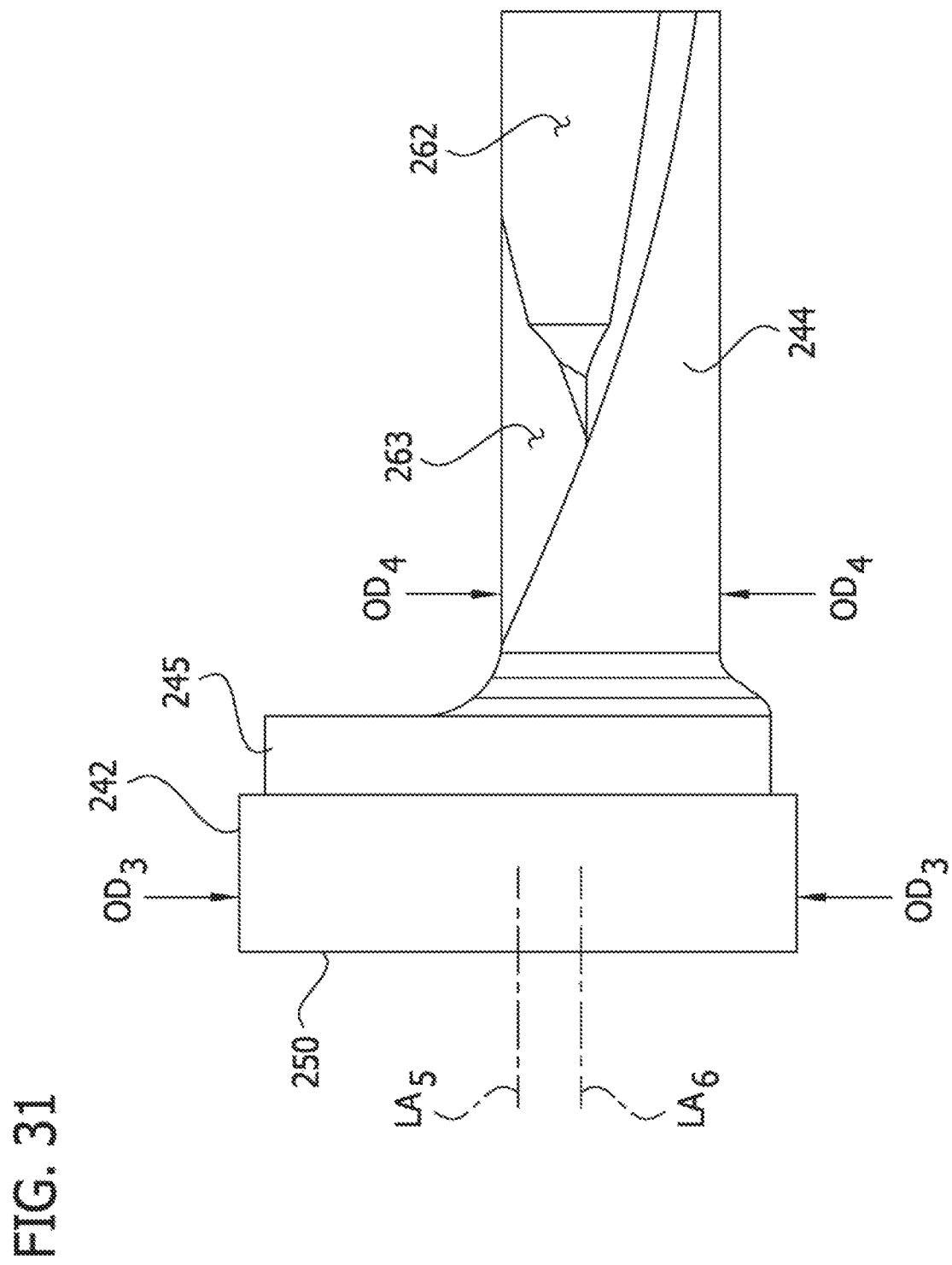
FIG. 31 is an enlarged side elevation of the cutter of FIG. 30.
Figure 32:
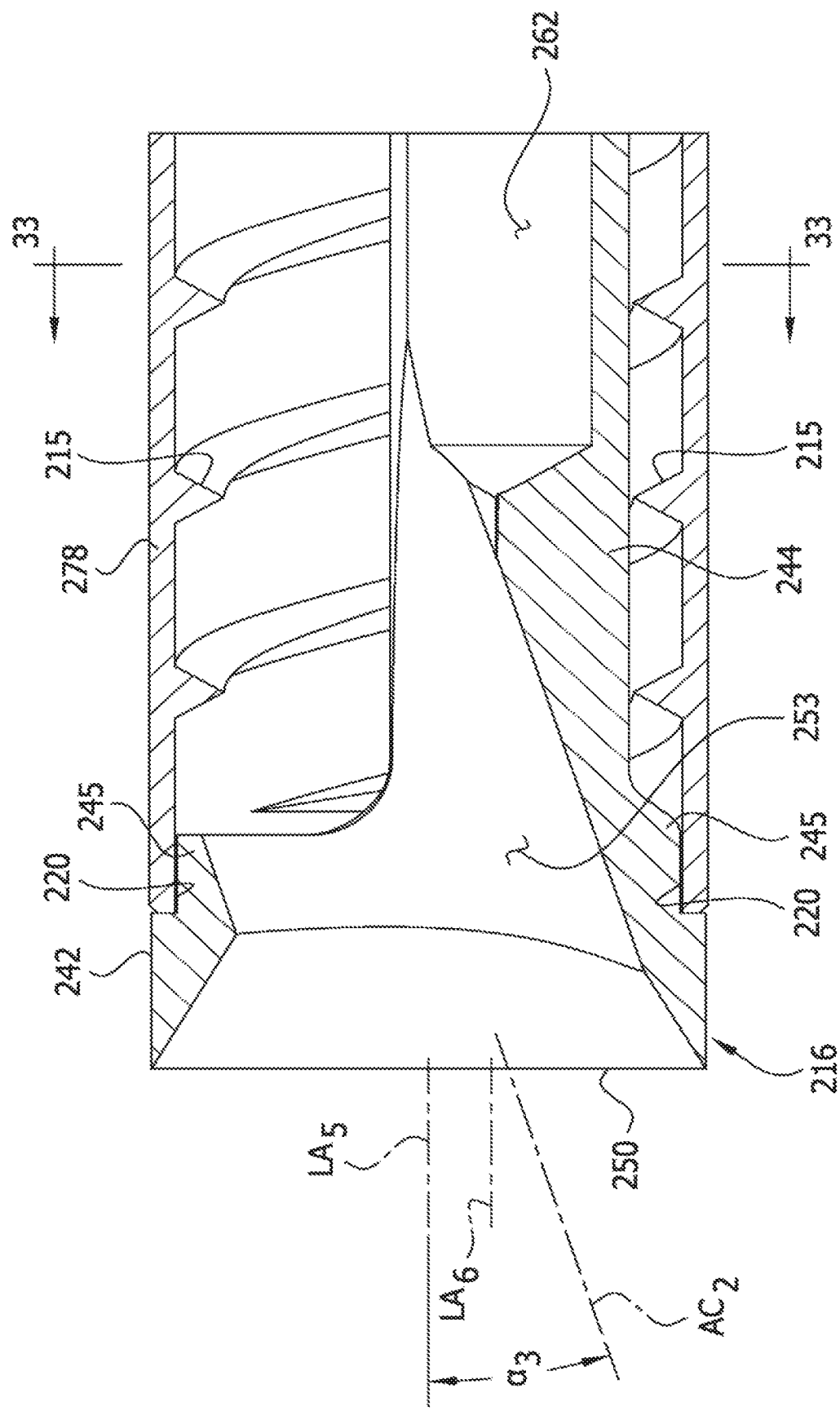
FIG. 32 is an enlarged longitudinal section of the cutter and a distal tube piece of the tissue-removing catheter of FIG. 28.
Figure 33:
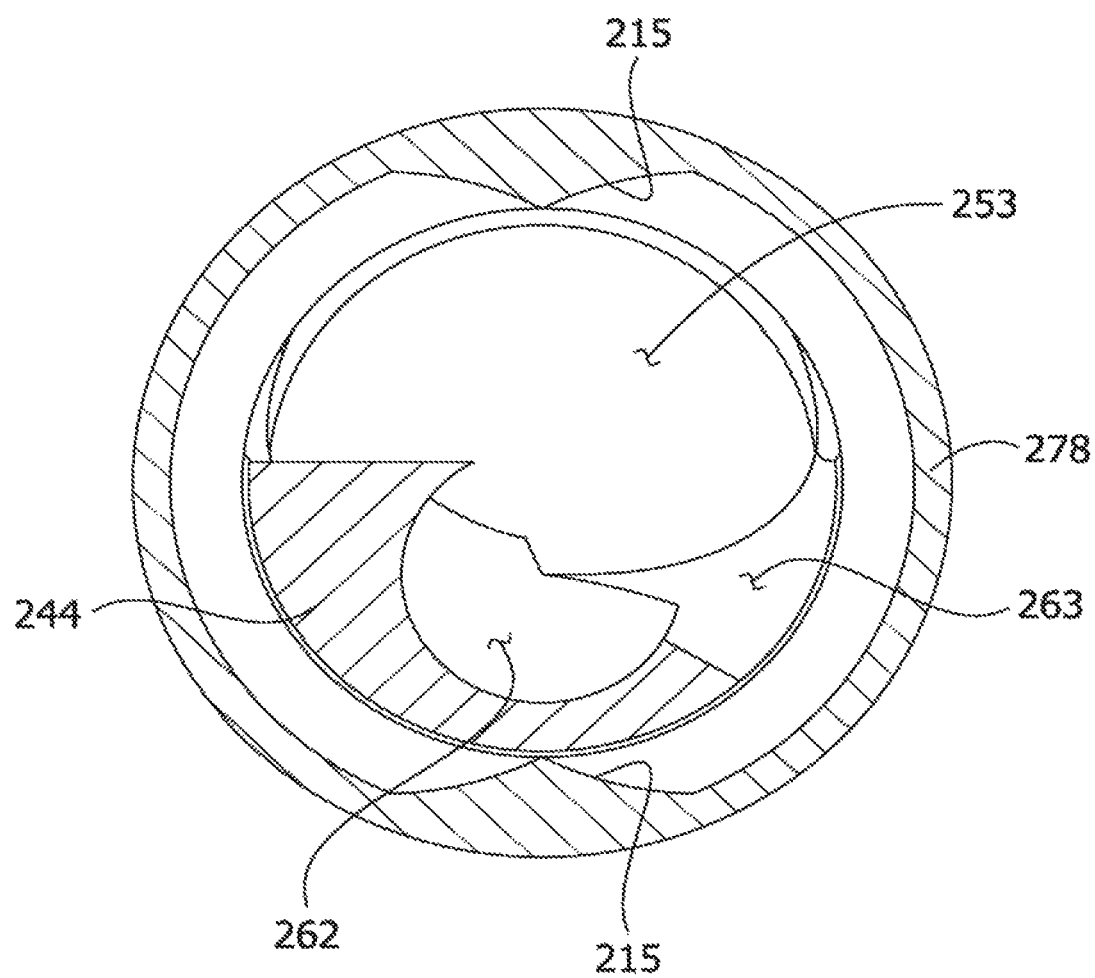
FIG. 33 is a cross section of the cutter and the distal tube piece taken through the plane indicated by the line 33-33 in FIG. 32.

Referring to FIGS. 31 and 32, the cutter 216 has opposite proximal and distal ends and a central longitudinal axis $LA_2$ extending therebetween. The cutter 216 has a generally cylindrical distal cutting portion 242, a proximal stem 244 (broadly, a driveshaft-connection portion) for connecting the cutter to the driveshaft 220, and a generally cylindrical bearing-engagement portion 245 intermediate the distal cutting portion and the stem. The distal cutting portion 242 has an outer cross-sectional dimension $OD_3$ (e.g., an outer diameter) that is greater than an outer cross-sectional dimension $OD_4$ (e.g., an outer diameter) of the stem 244, and the exterior of the bearing-engagement portion 245 steps down from the distal cutting portion. The cutter 216 may be formed as a single, one-piece construction, or may be formed from separate components secured to one another in a suitable manner, such as welding, soldering, adhesives, mechanical interference fit, threaded engagement and the like. As a non-limiting example, the cutter 216 may be comprised of steel, tungsten carbide, tungsten carbide cobalt, tungsten carbide molybdenum, silicon carbide, silicon nitride, ceramic, amorphous metals or other materials and may be manufactured by methods including turning, grinding, sintering, elector-discharge machining (EDM), laser cutting, heat treating, precipitation hardening, casting or other methods.

Referring to FIGS. 30-33, the distal cutting portion 242 of the cutter 116 includes an annular cutting tip 250 at the distal end thereof. The annular cutting tip 250 is co-axial with the central longitudinal axis $LA_5$; of the cutter 216. In one non-limiting example, the annular cutting tip 250 is beveled from an exterior surface of the cutter 216 toward the interior surface to define the sharp, distal cutting tip. The beveled, annular cutting tip 250 creates a "negative angle of attack," The beveled, annular cutting tip 250 may include raised elements (e.g., breakers), similar to those described above with respect to FIGS. 1-13, and/or flutes, similar to those described above with respect to FIGS. 14-16. The cutting tip 250 may be formed separately from the distal cutting portion 242 of cutter 216 and attached thereto, or the cutting tip may be formed integrally with the distal cutting portion of cutter. The cutting tip may be of other configurations without departing from the scope of the present invention.

Figure 29:
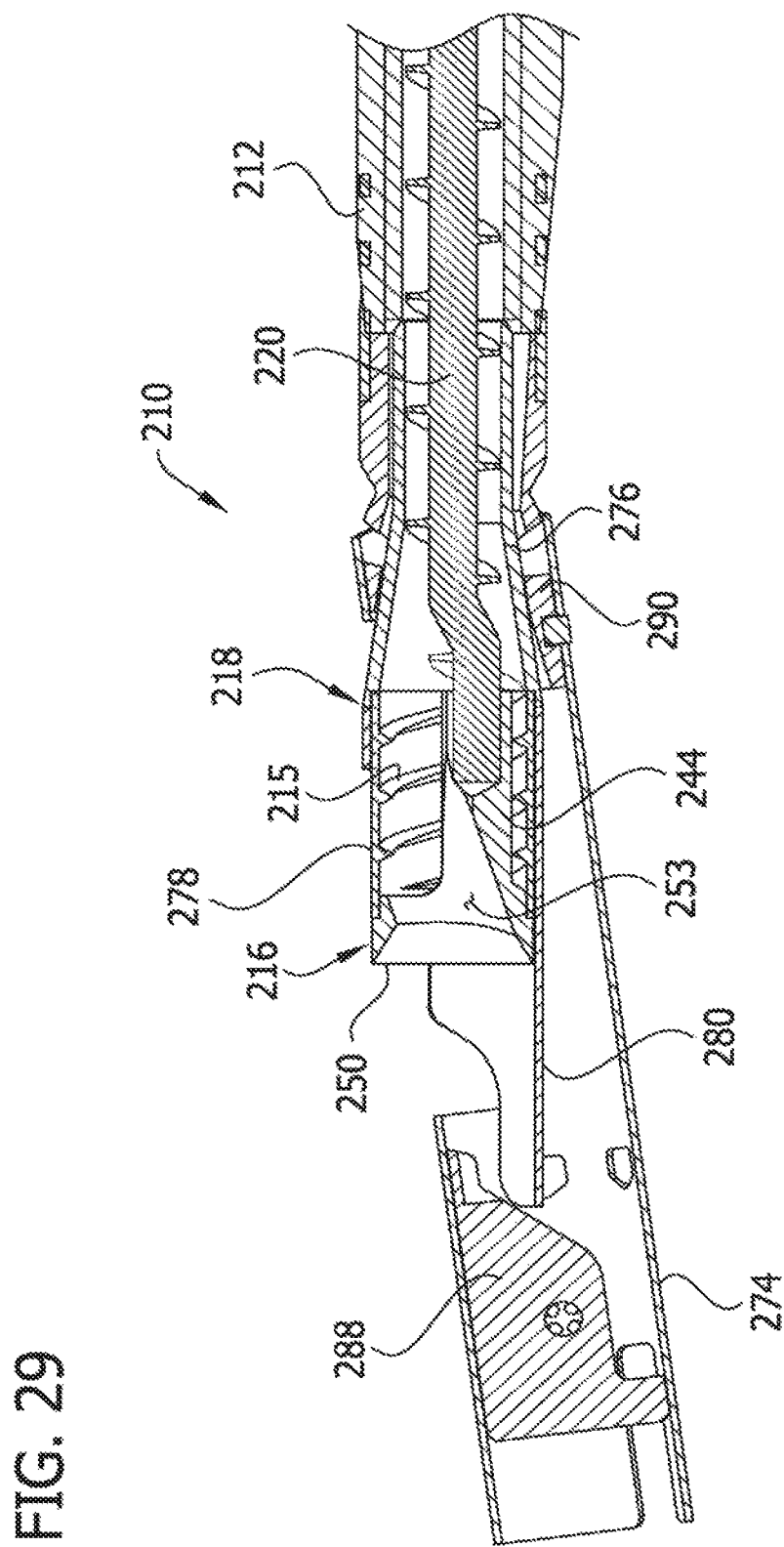
FIG. 29 is a longitudinal section of the distal end portion of the tissue-removing catheter of FIG. 28.
Figure 30:
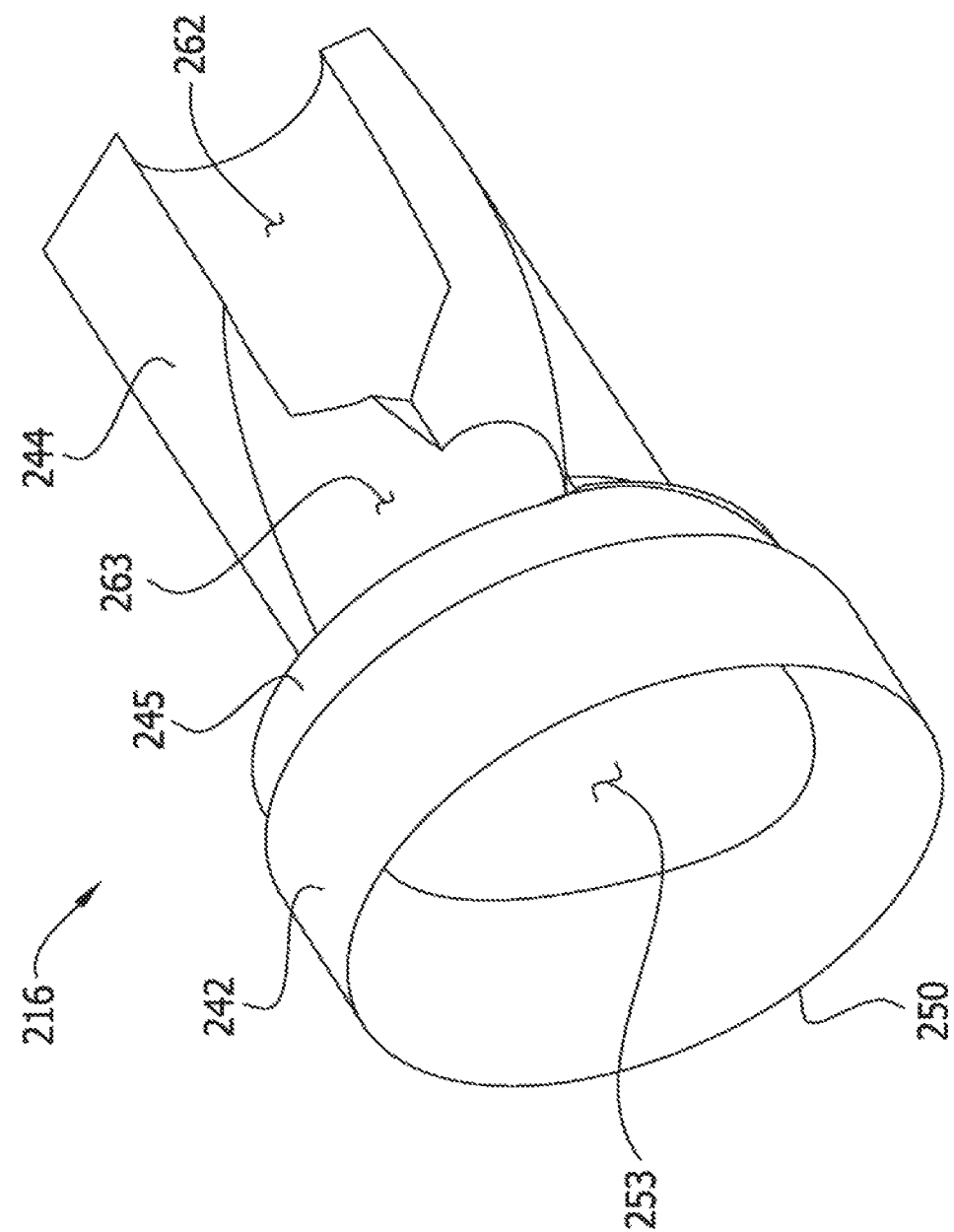
FIG. 30 is an enlarged front perspective of a cutter of the tissue-removing catheter of FIG. 2S.

Referring still to FIGS. 30-33, the stem 144 defines a bore 162 in which the distal end of the driveshaft 120 is secured (as shown in FIG. 29). For example, the distal end of the driveshaft 220 may be secured in the bore 262 by soldering, welding, adhesive, press-fit interference, crimping, or in other ways. The stem 244 and the bore 262 have coincident central longitudinal axes, both indicated by reference character $LA_5$ (see FIG. 31). For reasons set forth below, the central longitudinal axes of the stem 244 and the bore 262 are radially offset from the central longitudinal axis $LA_5$ of the cutter 216 (and the annular cutting tip 250). Accordingly, the rotational axis of the driveshaft 220 at the stem 244 is radially offset from the central longitudinal axis $LA_5$ of the cutter 216 (and the annular cutting tip 250). As explained below, although the rotational axis of the driveshaft 220 at the stem 244 is radially offset from the central longitudinal axis $LA_5$ of the cutter 216 (and the annular cutting tip 250), rotation of the driveshaft imparts rotation of the cutter and the annular cutting tip about the longitudinal axis $LA_5$ of the cutter (i.e., the rotational axis of the cutter is coincident with the longitudinal axis $LA_5$, of the cutter). In the illustrated embodiment, the offset stem 244 has a flute 263 (FIGS. 30, 31, and 33) extending along the length of the stem to facilitate proximal movement of the tissue as the tissue exits the cutter 216, as explained below.

Referring to FIGS. 29 and 32, the cutter 216 has an eccentric passage 253 (broadly, a tissue passage) extending from the annular cutting tip 250 through the stem 244. As shown in FIG. 32, the eccentric passage 253 has a central axis $AC_2$ that is angularly offset from the central longitudinal axis $LA_5$ of the cutter 216. As such, the tissue removed from the body lumen (e.g., blood vessel) by the cutting tip 250 passes through the cutter 216, via the eccentric passage 253, and into the cutter adaptor 218. A center $C_1$ is offset from the longitudinal axis $LA_5$ of the cutter 216. The central axis $AC_2$ of eccentric passage 253 may be angularly offset from the central longitudinal axis $LA_5$ of the cutter 214 by an angle which may measure from about 5 degrees to about 20 degrees. The eccentric opening 253 intersects the longitudinal axis $LA_5$. This can be accomplished because of the offset of the stem 244. As a result, the eccentric opening 253 can be larger than the eccentric opening 68 in the arrangement show in FIG. 9.

Referring to FIG. 32, the cutter 216 is received in the distal tube piece 278 of the cutter adaptor 218 such that the bearing-engagement portion 245 engages a distal end of the distal tube piece and an interior surface 220 of the distal tube piece. Thus, the distal tube piece 278 functions as a rotational bearing that allows for the cutter 216 to rotate about its central longitudinal axis $LA_5$ relative to the distal tube piece 278 (including the Other components of the cutter adaptor 218). Accordingly, although the rotational axis of the driveshaft 220 at the stem 244 is radially offset from the central longitudinal axis $LA_5$ of the cutter 216 (and the annular cutting tip 250), the cutter and the annular cutting tip rotate substantially about the longitudinal axis $LA_5$ of the cutter. Otherwise, the cutter 216 would rotate about the central longitudinal axis $LA_6$ of the stem 244, which would cause the cutting tip move along an elliptical path (i.e., wobble) relative to the catheter body 212.

Referring to FIGS. 29 and 32, the distal tube piece 278 includes an internal helical thread 215 extending along the length of the distal tube piece. Because the stem 244 is radially offset from the rotational axis of the cutter 216 (which is coincident with the central longitudinal axis $LA_5$ of the cutter), the stem of the cutter rides along the internal thread 215, in an eccentric or orbital motion, as the stem is rotated by the driveshaft 220. The interaction of the stem 244 with the thread 215 doves proximal movement of the removed tissue disposed in the distal tube piece 278. In other words, the stem 244 functions to push the removed tissue in the distal tube piece 278 against the internal thread 215, whereby the removed tissue moves proximally along the thread.

In an exemplary operation, the catheter 210 may be used in the same manner as set forth above with respect to catheter 10. However, instead of the stem 244 of the cutter 216 having an external thread to facilitate proximal movement of the removed tissue, the interaction of the internal thread 215 of the distal tube piece 278 and the eccentric stem 244 facilitates proximal movement of the removed tissue, as disclosed above.

Having described embodiments of the invention in detail, it will be apparent that modifications and variations are possible without departing from the scope of the invention defined in the appended claims.

When introducing elements of the present invention or the preferred embodiments(s) thereof, the articles "a", "an", "the" and said are intended to mean that there are one or more of the elements. The terms comprising, "including" and "having" are intended to be inclusive and mean that there may be additional elements other than the listed elements.

As various changes could be made in the above constructions, products, and methods without departing from the scope of the invention, it is intended that all matter contained in the above description and shown in the accompanying drawings shall be interpreted as illustrative and not hi a limiting sense.

What is claimed is:

1. A catheter for removing tissue from a body lumen, comprising:

an elongate catheter body configured for insertion into a body lumen of a subject, the catheter body having opposite distal and proximal ends, a longitudinal axis extending between the distal and proximal ends, and an interior passage extending along the longitudinal axis; and a cutter located generally at the distal end of the catheter body, the cutter having a proximal end portion, a distal end portion, and a longitudinal axis extending between the proximal and distal end portions, the cutter being rotatable relative to the catheter body generally about its longitudinal axis, the cutter including an annular cutting edge at the distal end portion of the cutter for removing tissue from the body lumen, an axial cavity defined by an interior surface of the cutter extending proximally from the annular cutting edge toward the proximal end portion of the cutter, and an eccentric opening extending from the axial cavity through the cutter to allow tissue removed from the body lumen by the annular cutting edge to pass proximally through the eccentric opening toward the interior passage of the catheter body, wherein the eccentric opening has an axis that is angularly offset from the longitudinal axis of the cutter;

wherein the eccentric opening has a first end that opens into the axial cavity and a second end that opens proximally through the cutter and wherein the eccentric opening extends longitudinally from the first end to the second end along the axis that is angularly offset from the longitudinal axis of the cutter.

2. The catheter set forth in claim 1, wherein the cutter has a transitional portion tapering toward the proximal end portion, wherein the eccentric opening extends through the transitional portion of the cutter.

3. The catheter set forth in claim 1, wherein the eccentric opening extends at an angle measuring from about 15 degrees to about 60 degrees offset from the longitudinal axis of the cutter.

4. The catheter set forth in claim 1, further comprising a driveshaft operatively connected to the proximal end portion of the cutter for selectively imparting rotation to the cutter.

5. The catheter set forth in claim 4, wherein the driveshaft is received in the interior passage of the catheter body and includes an external thread for transporting removed tissue proximally in the interior passage.

6. The catheter set forth in claim 5, wherein the cutter includes a stem at its proximal end portion having a central axis generally coincident with the longitudinal axis of the cutter, wherein the driveshaft is fixedly secured to the stem for imparting rotation to the cutter.

7. The catheter set forth in claim 6, wherein the stem includes an external thread for transporting removed tissue proximally toward the driveshaft.

8. The catheter set forth in claim 1, further comprising a stationary shearing edge adjacent to the eccentric opening in the cutter, wherein the cutter is rotatable relative to the stationary shearing edge to cut tissue passing proximally through the eccentric opening.

9. The catheter set forth in claim 8, wherein the cutter has a shearing edge partially defining the eccentric opening, the shearing edge of the cutter overlapping the stationary shearing edge in a radial direction relative to the longitudinal axis of the cutter as the cutter rotates to shear tissue passing proximally through the eccentric opening.

10. The catheter set forth in claim 9, further comprising a shearing member secured to the catheter body and defining the stationary shearing edge, wherein the shearing member has a bearing surface engaging an exterior of the cutter.

11. The catheter set forth in claim 10, wherein the stationary shearing edge is defined at the bearing surface.

12. The catheter set forth in claim 11, wherein the cutter includes a stem at its proximal end portion, the catheter further comprising a driveshaft operatively connected to the stem of the cutter for selectively imparting rotation to the cutter, wherein the stem and the driveshaft each includes an external thread for transporting removed tissue proximally in the interior passage of the catheter body.

13. The catheter set forth in claim 1, further comprising:
a deployment mechanism operatively connected to the cutter and the catheter body for selectively deploying and stowing the cutter, the deployment mechanism including
a camming element operatively connected to the cutter to allow for rotation of the cutter relative to the camming element, wherein the camming element is moveable axially with the cutter relative to the catheter body, and
a cutter housing hingedly attached adjacent the distal end of the catheter body, the cutter housing being pivotable about a hinge axis generally transverse to the longitudinal axis of the catheter body and having a cutter window,
wherein the deployment mechanism is configured such that:
proximal movement of the camming element relative to the catheter body and the cutter housing drives the cutter housing to pivot about the hinge axis so that the deployment mechanism opens, whereby the cutting edge extends through the cutter window and is exposed, and
distal movement of the camming element relative to the catheter body and the cutter housing drives the cutter housing to pivot about the hinge axis so that the deployment mechanism closes, whereby the cutting edge is stowed in the cutter housing and unexposed.

14. The catheter set forth in claim 13, wherein the camming element includes a tongue extending distally with respect to the annular cutting edge of the cutter, the cutter housing includes a closing ramp follower adjacent a distal end of the cutter housing, wherein the closing ramp follower is adapted to run along the tongue as the camming element is moved distally to facilitate closing of the deployment mechanism.

15. The catheter set forth in claim 14, wherein the cutter defines a tissue passage extending through the cutter from the annular cutting edge, wherein the camming element defines an internal passage in communication with the tissue passage of the cutter for receiving removed tissue passing through the cutter.

16. The catheter set forth in claim 15, wherein the internal passage defined by the camming element is in communication with the interior passage defined by the catheter body.

17. The catheter set forth in claim 14, wherein the tongue comprises a straight distal portion for guiding the cutter into the cutter housing and an arcuate portion to permit movement of the cutter housing to cover and expose the cutter.

18. The catheter set forth in claim 14, wherein the cutter housing further comprises an opening ramp follower disposed for driving the cutter housing to expose the cutter upon movement of the camming element in the proximal direction.

19. The catheter set forth in claim 18, wherein the opening ramp follower and closing ramp follower remain in operative contact with the camming element in all relative positions of the cutter housing and camming element.

20. The catheter set forth in claim 1, further comprising:
a guard disposed immediately distal of the annular cutting edge of the cutter, the guard configured to cover at least about one half of a circumferential portion of the annular cutting edge to inhibit tissue removed from the body lumen and disposed in the axial cavity from exiting the cutter distally through the annular cutting edge.

* * * * *